(12) United States Patent
Liang et al.

(10) Patent No.: US 10,202,367 B2
(45) Date of Patent: Feb. 12, 2019

(54) HETEROCYCLIC COMPOUNDS AND METHODS OF USE THEREOF

(71) Applicants: The United States of America, as represented by the Secretary, Department of Health and Human Services, Washington, DC (US); University of Kansas, Lawrence, KS (US)

(72) Inventors: Tsanyang Liang, Potomac, MD (US); Zongyi Hu, Potomac, MD (US); Juan Jose Marugan, Gaithersburg, MD (US); Noel Terrence Southall, Potomac, MD (US); Shanshan He, North Bethesda, MD (US); Xin Hu, Frederick, MD (US); Jingbo Xiao, Rockville, MD (US); Marc Ferrer, Potomac, MD (US); Wei Zheng, Potomac, MD (US); Kevin J. Frankowski, Lawrence, KS (US); Frank J. Schoenen, Lawrence, KS (US); Kelin Li, Lawrence, KS (US)

(73) Assignees: The United States of America, as represented by the Secretary, Department of Health and Human Services, Washington, DC (US); University of Kansas, Lawrence, KS (US)

( * ) Notice: Subject to any disclaimer, the term of this patent is extended or adjusted under 35 U.S.C. 154(b) by 0 days.

(21) Appl. No.: 15/317,864

(22) PCT Filed: Jun. 12, 2015

(86) PCT No.: PCT/US2015/035658
§ 371 (c)(1),
(2) Date: Dec. 9, 2016

(87) PCT Pub. No.: WO2015/192077
PCT Pub. Date: Dec. 17, 2015

(65) Prior Publication Data
US 2017/0114053 A1    Apr. 27, 2017

Related U.S. Application Data

(60) Provisional application No. 62/011,462, filed on Jun. 12, 2014.

(51) Int. Cl.
*C07D 413/14* (2006.01)
*A61K 31/4545* (2006.01)
(Continued)

(52) U.S. Cl.
CPC ........ *C07D 413/06* (2013.01); *A61K 31/4178* (2013.01); *A61K 31/454* (2013.01); *A61K 31/4545* (2013.01); *A61K 31/496* (2013.01); *A61K 31/5377* (2013.01); *A61K 31/7056* (2013.01); *A61K 31/7068* (2013.01); *A61K 38/07* (2013.01); *A61K 38/13* (2013.01);
(Continued)

(58) Field of Classification Search
CPC .................................................... C07D 413/14
See application file for complete search history.

(56) References Cited

U.S. PATENT DOCUMENTS

| | | | |
|---|---|---|---|
| 2009/0163545 A1* | 6/2009 | Goldfarb | A61K 31/122 514/312 |
| 2011/0301149 A1* | 12/2011 | Wu | A61K 31/4162 514/217.05 |

FOREIGN PATENT DOCUMENTS

| | | |
|---|---|---|
| WO | 2004/103996 A1 | 12/2004 |
| WO | 2009/086303 A2 | 7/2009 |

OTHER PUBLICATIONS

CA registry No. 902500-07-6, entered into CA registry File on Aug. 17, 2006, supplied by Aurora Fine Chemicals.*
(Continued)

*Primary Examiner* — Emily A Bernhardt
(74) *Attorney, Agent, or Firm* — Leydig, Voit & Mayer, Ltd.

(57) ABSTRACT

Disclosed are compounds of formula (I), formula (II), and formula (III): wherein Ar, $R^1$, A, and X are as defined in the specification. These compounds are antiviral agents and are contemplated for use in the treatment of viral infections, for example, hepatitis C. These compounds are also contemplated for use in treating or preventing cancers.

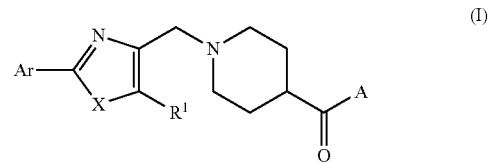

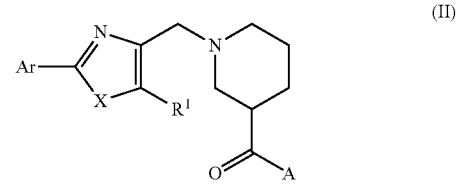

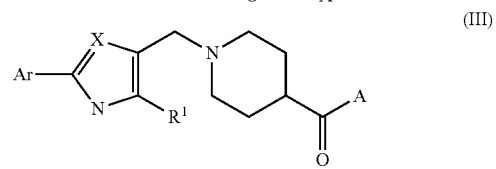

6 Claims, 3 Drawing Sheets

Figure 1A:
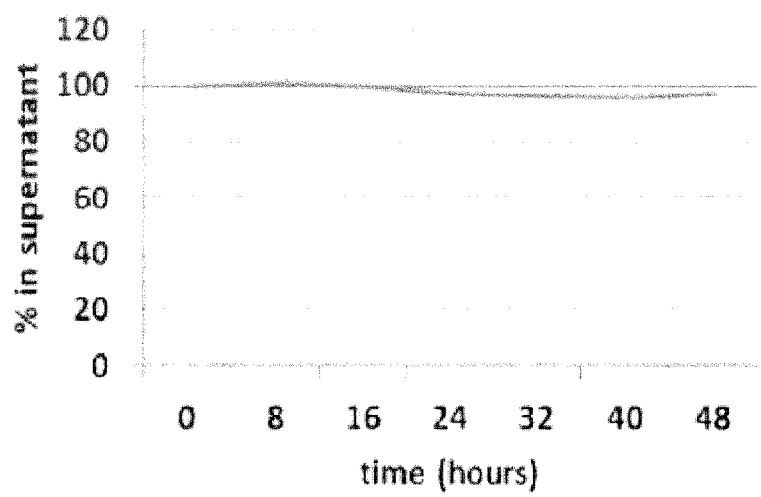

(51) Int. Cl.

| | |
|---|---|
| *C07D 417/14* | (2006.01) |
| *C07D 471/08* | (2006.01) |
| *A61K 31/496* | (2006.01) |
| *A61K 31/5377* | (2006.01) |
| *C07D 413/06* | (2006.01) |
| *A61K 31/4178* | (2006.01) |
| *A61K 31/454* | (2006.01) |
| *A61K 31/7056* | (2006.01) |
| *A61K 31/7068* | (2006.01) |
| *A61K 38/07* | (2006.01) |
| *A61K 38/13* | (2006.01) |
| *A61K 38/21* | (2006.01) |

(52) U.S. Cl.
CPC .......... *A61K 38/212* (2013.01); *C07D 413/14* (2013.01); *C07D 417/14* (2013.01); *C07D 471/08* (2013.01); *Y02A 50/385* (2018.01)

(56) References Cited

OTHER PUBLICATIONS

Aurora Fine Chemicals Product Guide.1 page, retrieved from the Internet at http://www.aurorafinechemicals.com/abouthtml on Apr. 28, 2015.*
Goldfarb I, Chemical Abstracts vol. 151. No. 92849 and 92847, abstracts for US 2009/0163545 (2009).*
Goldfarb II, Chemical Abstracts vol. 151. No. 92845,92840,70320, abstracts for US 2009/0163545 (2009).*
Masaki et al., "Production of Infectious Hepatitis C Virus by Using RNA Polymerase I-Mediated Transcription" *Journal of Virology*, 84:5824-5835 (2010).
International Searching Authority, International Search Report in Patent Application No. PCT/US2015/035658, dated Aug. 19, 2015.
International Searching Authority, Written Opinion in Patent Application No. PCT/US2015/035658, dated Aug. 19, 2015.
International Preliminary Report on Patentability, Patent Application No. PCT/US2015/035658, dated Jun. 6, 2016.

* cited by examiner

HETEROCYCLIC COMPOUNDS AND METHODS OF USE THEREOF

CROSS REFERENCE TO RELATED APPLICATIONS

This patent application is a U.S. National Phase of International Patent Application No. PCT/US2015/035658, filed Jun. 12, 2015, which claims the benefit of U.S. Provisional Patent Application No. 62/011,462, filed Jun. 12, 2014, the disclosures of which are incorporated by reference for all purposes.

STATEMENT REGARDING FEDERALLY SPONSORED RESEARCH OR DEVELOPMENT

This invention was made with government support under grant number U54 HG005031 awarded by the National Institutes of Health. The government has certain rights in the invention.

BACKGROUND OF THE INVENTION

Hepatitis C virus (HCV) infects about 200 million people in the world. Many infected people progress to chronic liver disease including cirrhosis with a risk of developing liver cancer. To date, there is no effective vaccine for hepatitis C.

Current standard treatment of chronic hepatitis C, based on combination of peginterferon-α and ribavirin, is only effective in about half of the patients, with significant adverse effects. The fraction of people with HCV who can complete a successful treatment is estimated to be no more than 10 percent. Recent development of direct-acting antivirals against HCV, such as protease and polymerase inhibitors, is promising but still requires combination with peginterferon and ribavirin for maximal efficacy. In addition, these agents are associated with high rates of resistance and many have significant side effects.

In view of the foregoing, an unmet need exists for novel agents for treating or preventing viral infection.

BRIEF SUMMARY OF THE INVENTION

The invention provides a compound of formula (I), formula (II), or formula (III):

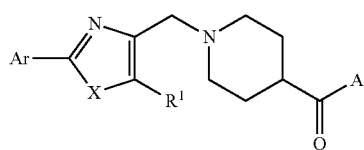

(I)

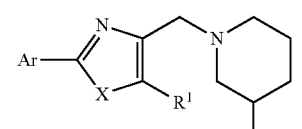

(II)

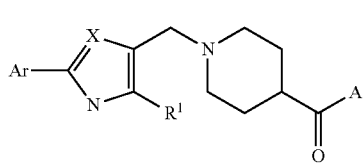

(III)

wherein Ar is optionally substituted $C_6$-$C_{14}$ aryl,
X is O or S,
$R^1$ is hydrogen, $C_1$-$C_6$ alkyl, or $CF_3$,
A is

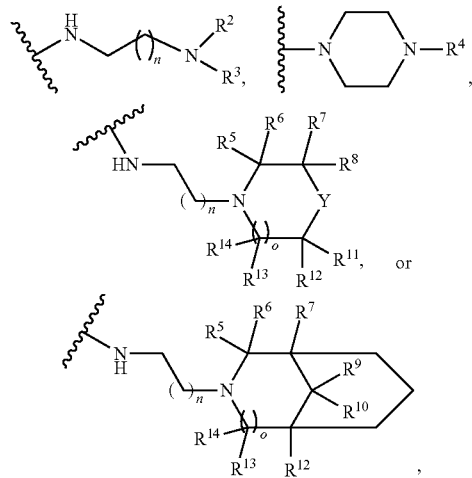

wherein n is an integer of 1 to 3,
o is 0 or 1,
Y is $CR^9R^{10}$ or O,
$R^2$ and $R^3$ are independently $C_1$-$C_6$ alkyl,
$R^4$ is di($C_1$-$C_6$ alkylamino)$C_2$-$C_6$ alkyl or a 5- or 6-membered N-containing heterocyclic ring, and
$R^5$-$R^{14}$ are independently hydrogen or $C_1$-$C_6$ alkyl,
or a pharmaceutically acceptable salt thereof, stereoisomer thereof, or mixture comprising stereoisomers thereof.

The invention also provides a method of treating or preventing hepatitis C comprising administering to a mammal in need thereof an effective amount of a compound of formula (I), formula (II), or formula (III):

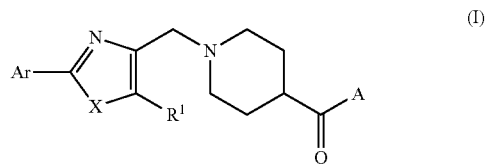

(I)

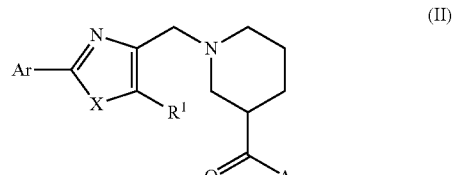

(II)

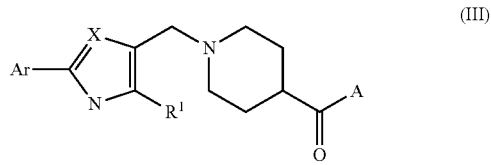

(III)

wherein Ar is optionally substituted $C_6$-$C_{14}$ aryl,
X is O or S,
$R^1$ is hydrogen, $C_1$-$C_6$ alkyl, or $CF_3$, A is

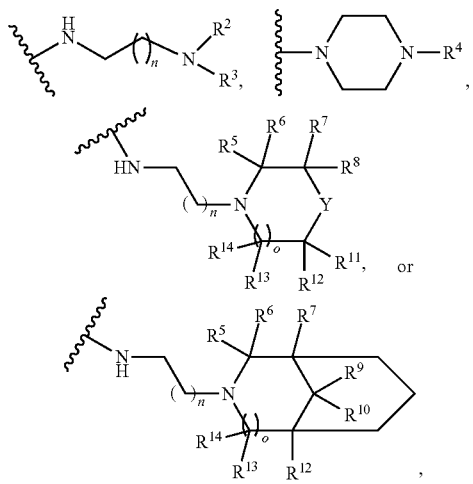

wherein n is an integer of 1 to 3,
o is 0 or 1,
Y is $CR^9R^{10}$ or O,
$R^2$ and $R^3$ are independently $C_1$-$C_6$ alkyl,
$R^4$ is di($C_1$-$C_6$ alkylamino)$C_2$-$C_6$ alkyl or a 5- or 6-membered N-containing heterocyclic ring, and
$R^5$-$R^{14}$ are independently hydrogen or $C_1$-$C_6$ alkyl,
or a pharmaceutically acceptable salt thereof, stereoisomer thereof, or mixture comprising stereoisomers thereof.

The invention further provides a method for synergistically enhancing the antiviral effect of an anti-hepatitis C compound in a mammal undergoing treatment with the anti-hepatitis C compound, comprising administering to the mammal a compound of formula (I), formula (II), or formula (III):

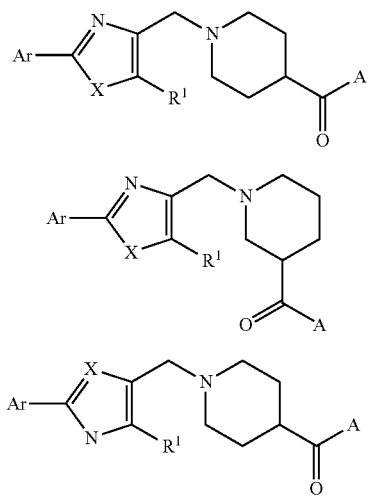

wherein Ar is optionally substituted $C_6$-$C_{14}$ aryl,
X is O or S,
$R^1$ is hydrogen, $C_1$-$C_6$ alkyl, or $CF_3$, A is

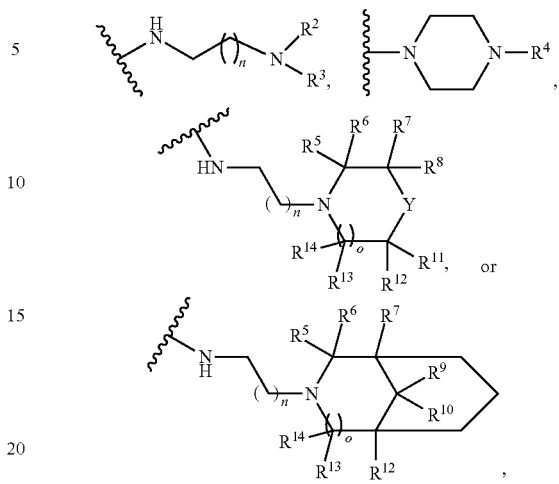

wherein n is an integer of 1 to 3,
o is 0 or 1,
Y is $CR^9R^{10}$ or O,
$R^2$ and $R^3$ are independently $C_1$-$C_6$ alkyl,
$R^4$ is di($C_1$-$C_6$ alkylamino)$C_2$-$C_6$ alkyl or a 5- or 6-membered N-containing heterocyclic ring, and
$R^5$-$R^{14}$ are independently hydrogen or $C_1$-$C_6$ alkyl,
or a pharmaceutically acceptable salt thereof, stereoisomer thereof, or mixture comprising stereoisomers thereof,
in combination with the anti-hepatitis C compound.

The invention additionally provides a kit comprising:
(a) a compound of formula (I), formula (II), or formula (III):

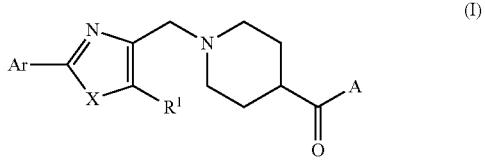

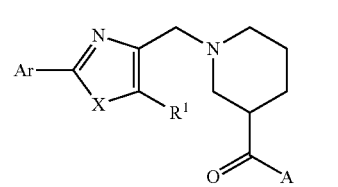

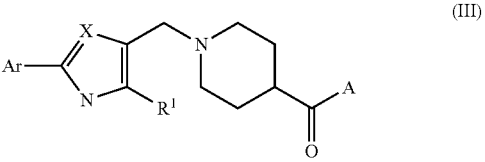

wherein Ar is optionally substituted $C_6$-$C_{14}$ aryl,
X is O or S,
$R^1$ is hydrogen, $C_1$-$C_6$ alkyl, or $CF_3$,
A is

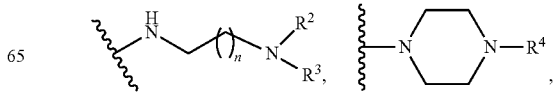

-continued

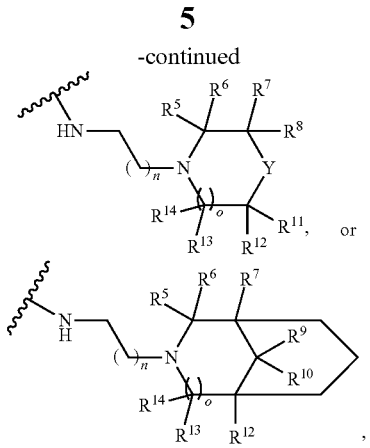

wherein n is an integer of 1 to 3,
o is 0 or 1,
Y is $CR^9R^{10}$ or O,
$R^2$ and $R^3$ are independently $C_1$-$C_6$ alkyl,
$R^4$ is di($C_1$-$C_6$ alkylamino)$C_2$-$C_6$ alkyl or a 5- or 6-membered N-containing heterocyclic ring, and
$R^5$-$R^{14}$ are independently hydrogen or $C_1$-$C_6$ alkyl,
or a pharmaceutically acceptable salt thereof, stereoisomer thereof, or mixture comprising stereoisomers thereof, and (b) an anti-hepatitis C compound other than a compound of formula (II).

The invention also provides a method of treating or preventing cancer in a mammal in need thereof comprising administering to a mammal in need thereof an effective amount of a compound of formula (I), formula (II), or formula (III):

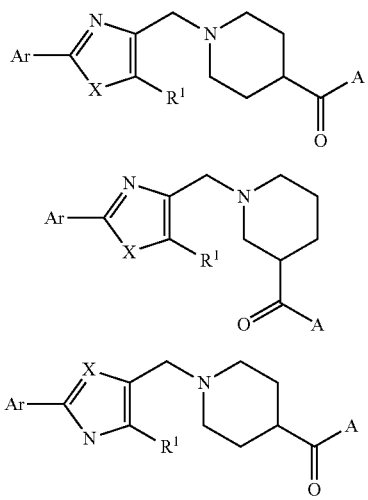

wherein Ar is optionally substituted $C_6$-$C_{14}$ aryl,
X is O or S,
$R^1$ is hydrogen, $C_1$-$C_6$ alkyl, or $CF_3$,
A is

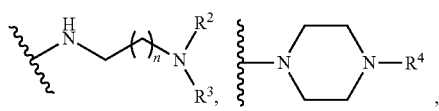

-continued

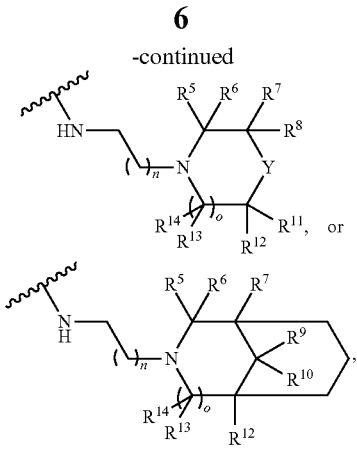

wherein n is an integer of 1 to 3,
o is 0 or 1,
Y is $CR^9R^{10}$ or O,
$R^2$ and $R^3$ are independently $C_1$-$C_6$ alkyl,
$R^4$ is di($C_1$-$C_6$ alkylamino)$C_2$-$C_6$ alkyl or a 5- or 6-membered N-containing heterocyclic ring, and
$R^5$-$R^{14}$ are independently hydrogen or $C_1$-$C_6$ alkyl,
or a pharmaceutically acceptable salt thereof, stereoisomer thereof, or mixture comprising stereoisomers thereof.

BRIEF DESCRIPTION OF THE SEVERAL VIEWS OF THE DRAWING(S)

Figure 1B:
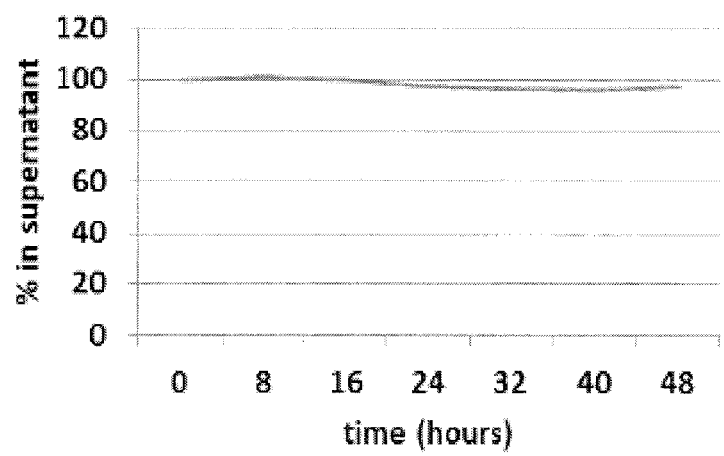
Figure 2A:
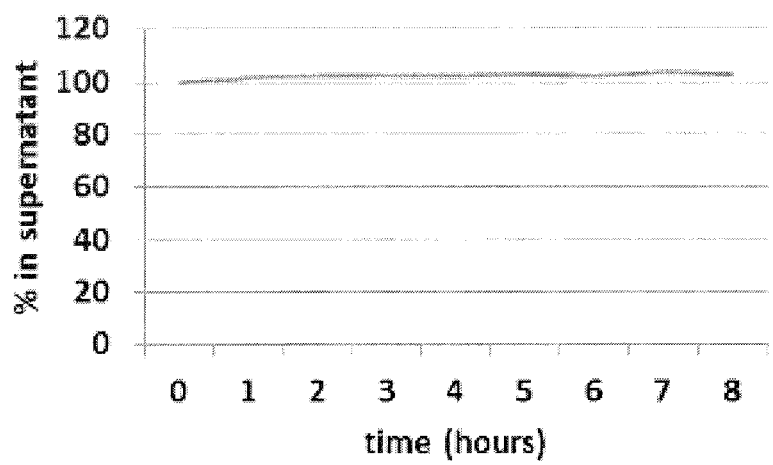
Figure 2B:
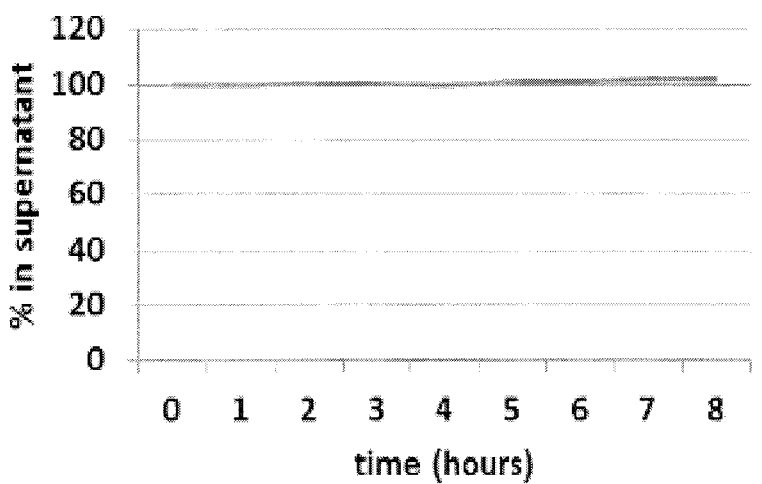
Figure 3:
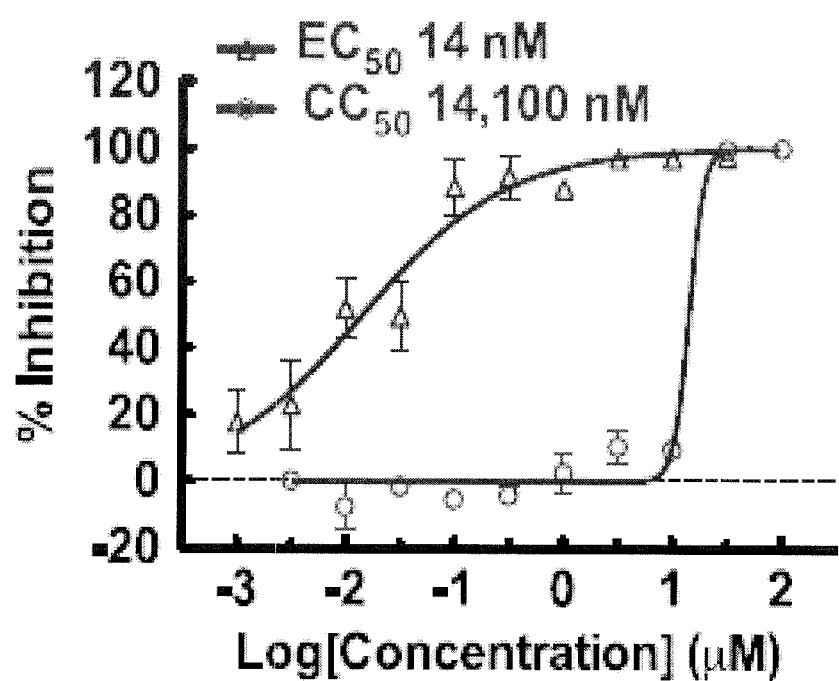

FIG. 1A depicts the stability of compound 1 in PBS.
FIG. 1B depicts the stability of compound 1 in PBS/acetonitrile (1/1).
FIG. 2A depicts the stability of compound 1 in PBS in the presence of 50 µM dithiothreitol.
FIG. 2B depicts the stability of compound 1 in PBS/acetonitrile (1/1) PBS in the presence of 50 µM dithiothreitol.
FIG. 3 depicts titration curves for anti-HCV activity ($EC_{50}$ shown by triangles) and cytotoxicity ($CC_{50}$ shown by circles) of compound 1.

DETAILED DESCRIPTION OF THE INVENTION

In an embodiment, the invention provides a compound of formula (I), formula (II), or formula (III):

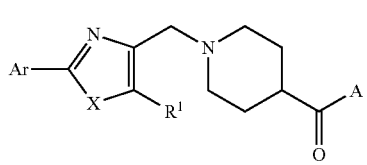

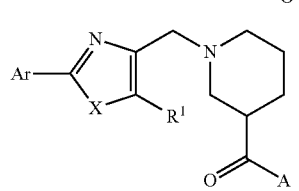

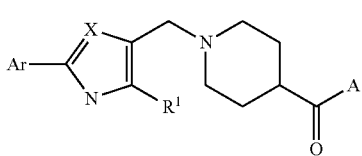

(III)

wherein Ar is optionally substituted $C_6$-$C_{14}$ aryl,
X is O or S,
$R^1$ is hydrogen, $C_1$-$C_6$ alkyl, or $CF_3$,
A is

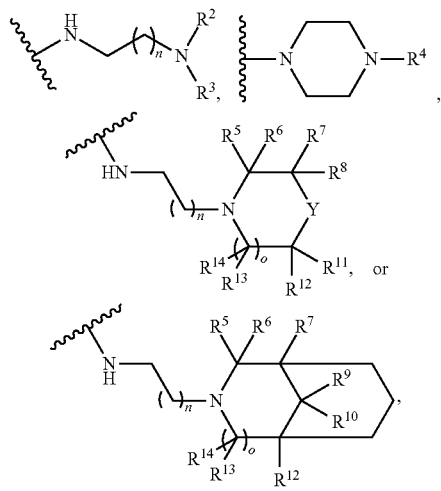

wherein n is an integer of 1 to 3,
o is 0 or 1,
Y is $CR^9R^{10}$ or O,
$R^2$ and $R^3$ are independently $C_1$-$C_6$ alkyl,
$R^4$ is di($C_1$-$C_6$ alkylamino)$C_2$-$C_6$ alkyl or a 5- or 6-membered N-containing heterocyclic ring, and
$R^5$-$R^{14}$ are independently hydrogen or $C_1$-$C_6$ alkyl,
or a pharmaceutically acceptable salt thereof, stereoisomer thereof, or mixture comprising stereoisomers thereof.

Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tort-butyl, pentyl, isoamyl, hexyl, and the like.

The term "alkoxy" means a straight-chain or branched alkoxy substituent containing from, for example, 1 to about 6 carbon atoms, preferably from 1 to about 4 carbon atoms, more preferably from 1 to 2 carbon atoms. Examples of such substituents include methoxy, ethoxy, propoxy, isopropoxy, n-butoxy, sec-butoxy, isobutoxy, tert-butoxy, pentoxy, isoamyoxyl, hexyloxy, and the like.

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{14}$ aryl" includes phenyl, naphthyl, and anthracenyl. It is understood that the term aryl applies to cyclic substituents that are planar and comprise $4n+2$ π electrons, according to Hückel's Rule.

Whenever a range of the number of atoms in a structure is indicated (e.g., a $C_1$-$C_{12}$, $C_1$-$C_8$, $C_1$-$C_6$, $C_1$-$C_4$, or $C_2$-$C_{12}$, $C_2$-$C_8$, $C_2$-$C_6$, $C_2$-$C_4$ alkyl, alkoxy, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate). Similarly, the recitation of a range of 6-14 carbon atoms (e.g., $C_6$-$C_{14}$) as used with respect to any chemical group (e.g., aryl) referenced herein encompasses and specifically describes 6, 7, 8, 9, 10, 11, 12, 13, and/or 14 carbon atoms, as appropriate, as well as any sub-range thereof (e.g., 6-14 carbon atoms, 6-13 carbon atoms, 6-12 carbon atoms, 6-11 carbon atoms, 6-10, 7-10 carbon atoms, 7-9 carbon atoms, 7-8 carbon atoms, 8-10 carbon atoms, and/or 8-9 carbon atoms, etc., as appropriate).

In certain embodiments, Ar is phenyl optionally substituted with one or more substituents selected from $C_1$-$C_6$ alkyl, $C_1$-$C_6$ alkoxy, halo, and $CF_3$.

In certain preferred embodiments, Ar is selected from 2-methylphenyl, 3,5-dimethoxyphenyl, 2-chlorophenyl, 2-chloro-6-methylphenyl, 4-chlorophenyl, 2-ethylphenyl, 3-methylphenyl, 4-methylphenyl, 3,4-dimethylphenyl, 2,6-dimethylphenyl, 3-chlorophenyl, 3-methyl-4-fluorophenyl, 3,5-di(trifluoromethyl)phenyl, 2,4-dimethylphenyl, 3,5-dimethylphenyl, 2-chloro-6-fluorophenyl, 2,5-dimethylphenyl, 2,6-dichlorophenyl, 2-fluoro-6-methoxyphenyl, 2-bromo-6-methoxyphenyl, 2-bromo-6-chlorophenyl, 2,6-dibromophenyl, 2-chloro-6-trifluoromethylphenyl, 2-methyl-6-methoxyphenyl, 2-fluoro-6-methylphenyl, 2,6-difluorophenyl, 3,4-dichlorophenyl, 4-fluorophenyl, 2,3,4,5,6-pentamethylphenyl, and 2,4,6-trimethylphenyl.

In certain embodiments, the compound is of formula (I).

In certain embodiments, A is

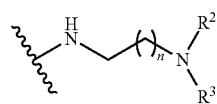

and $R^2$ and $R^3$ are independently $C_1$-$C_6$ alkyl.

In certain particular embodiments, the compound is:
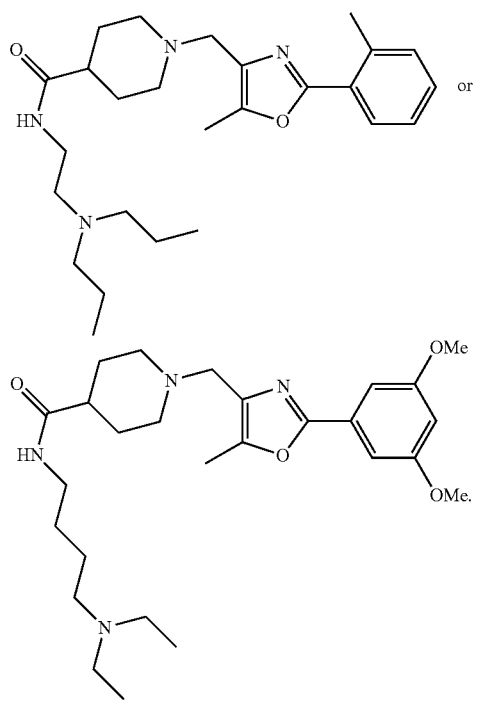
or
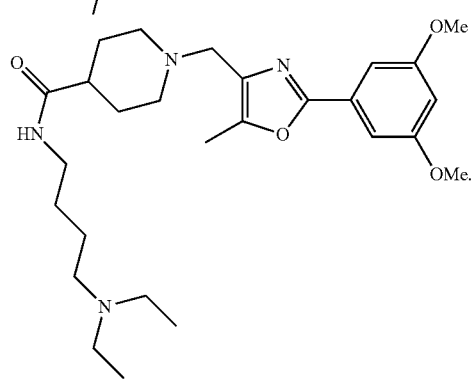
In certain embodiments, A is
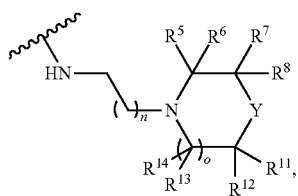
Y is CR$^9$R$^{10}$, and R$^5$-R$^{14}$ are independently hydrogen or C$_1$-C$_6$ alkyl.
In certain preferred embodiments, A is selected from:
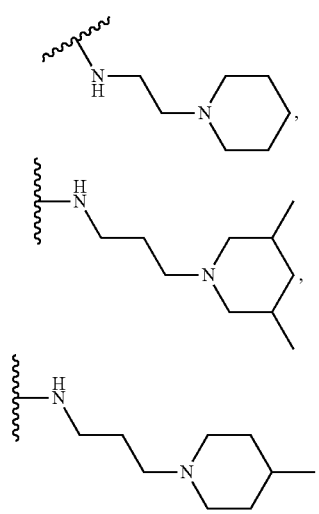
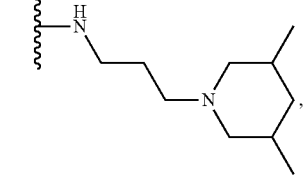
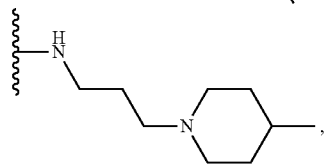
-continued
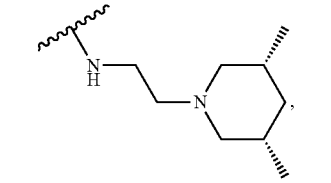
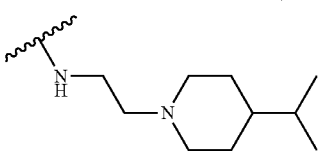
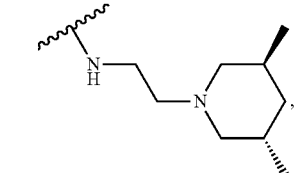
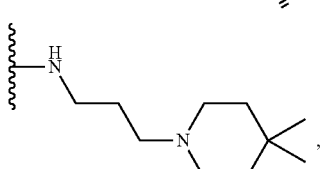
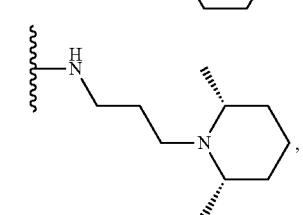
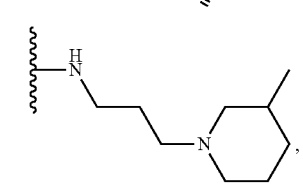
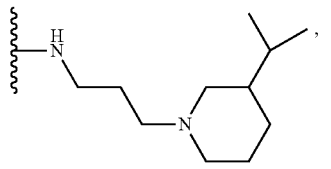
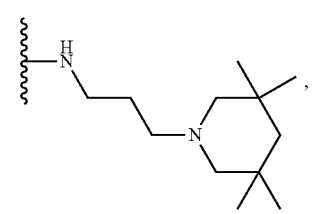

-continued
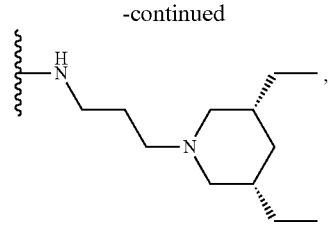
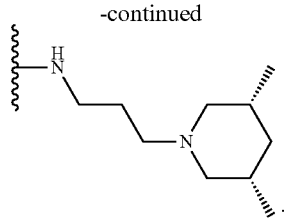
In a particular embodiment, when Ar is 2-methylphenyl or 2-chloro-6-methylphenyl and $R^1$ is methyl, A is not
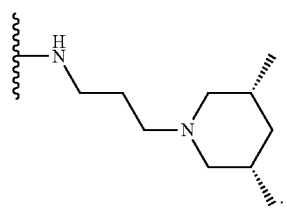 [SMILES: *NCCCN1C[C@H](C)C[C@H](C)C1]
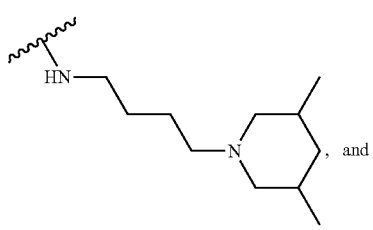, and
In certain particular embodiments, the compound is selected from:
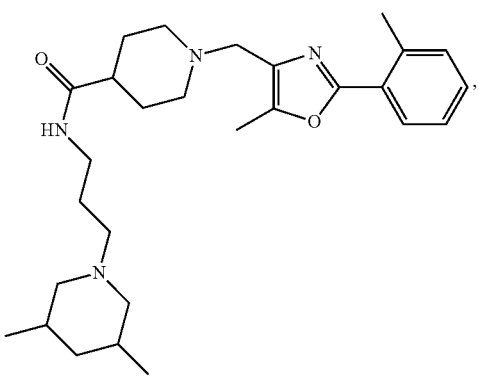
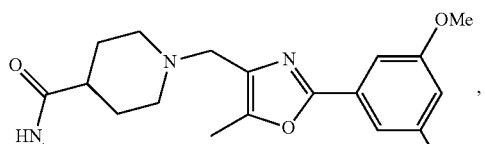
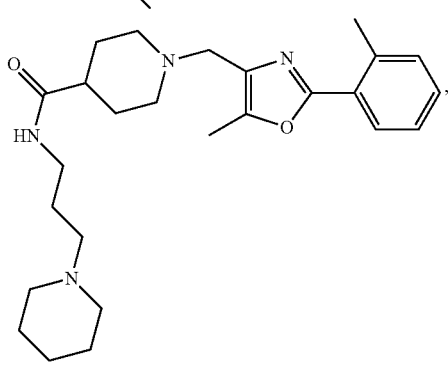
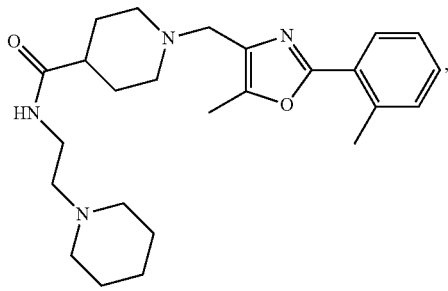
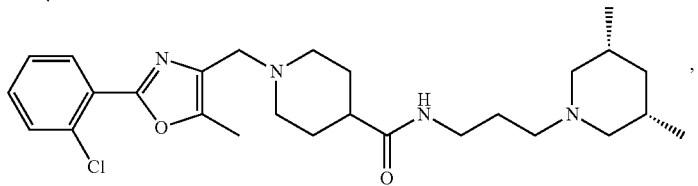

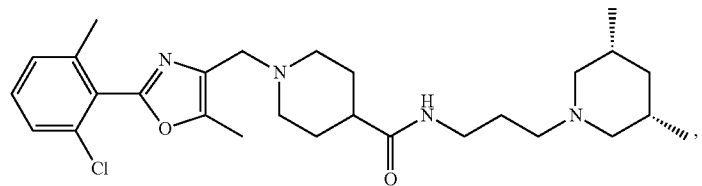
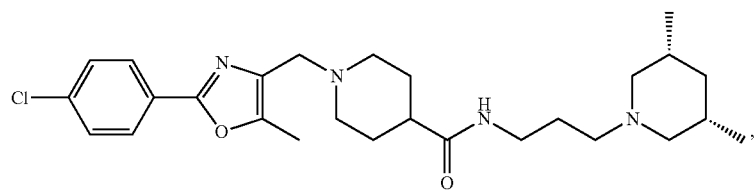
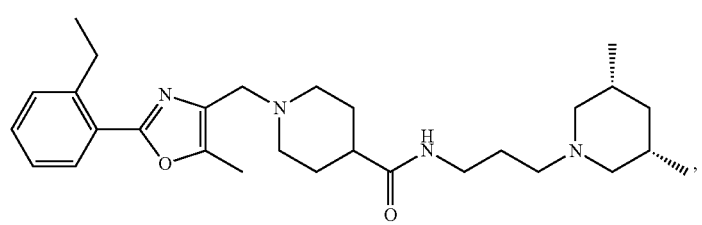
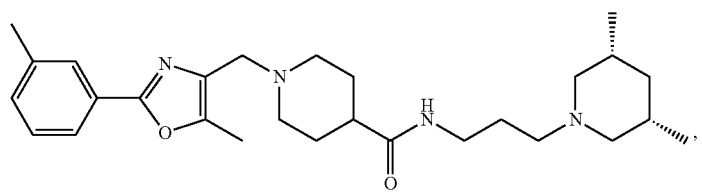
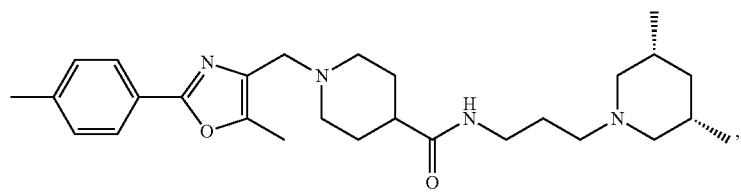
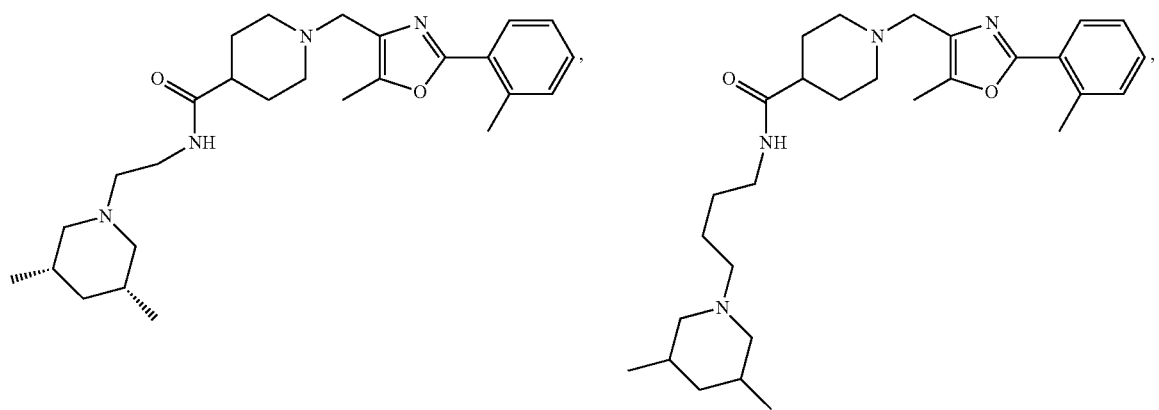

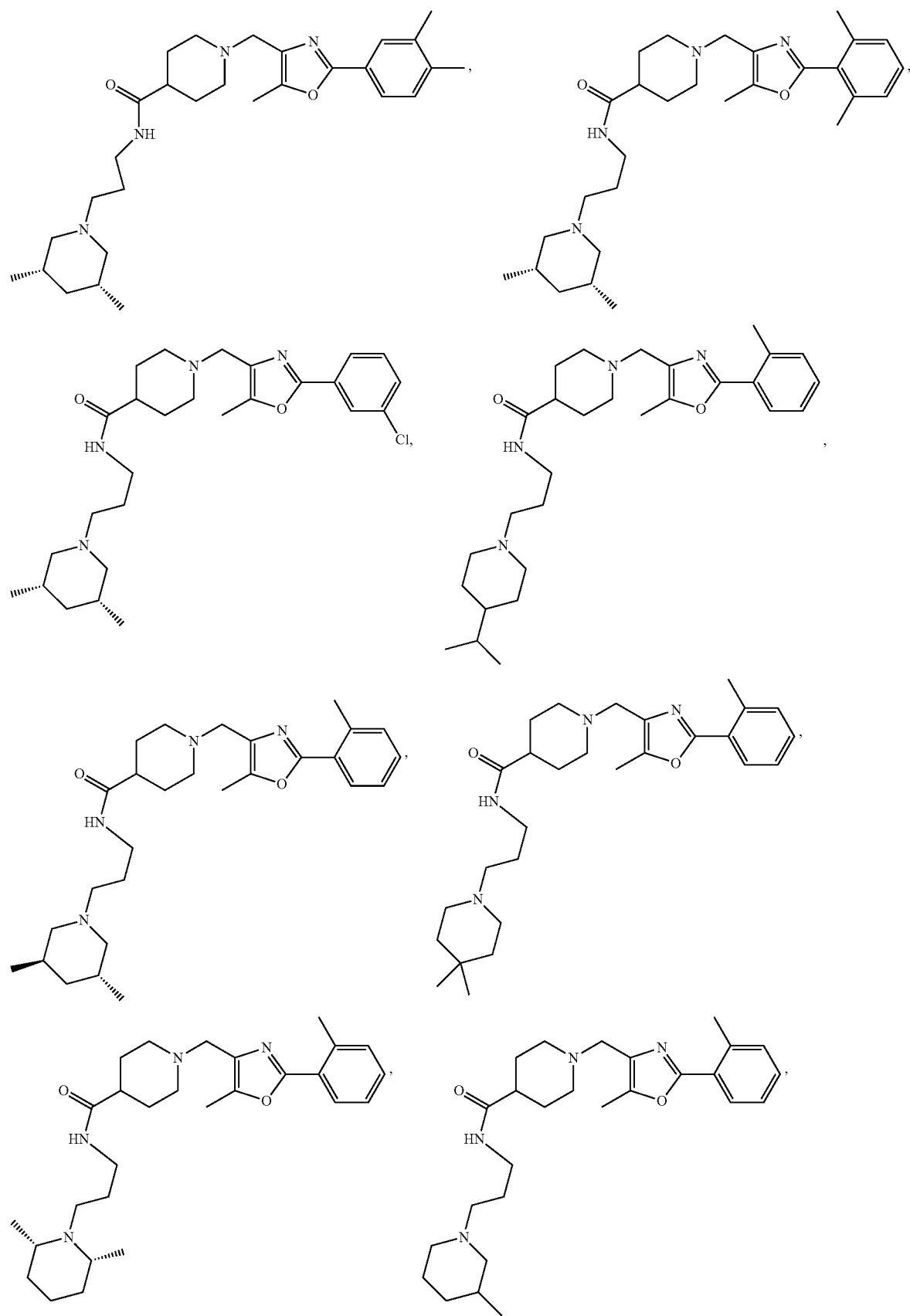

-continued
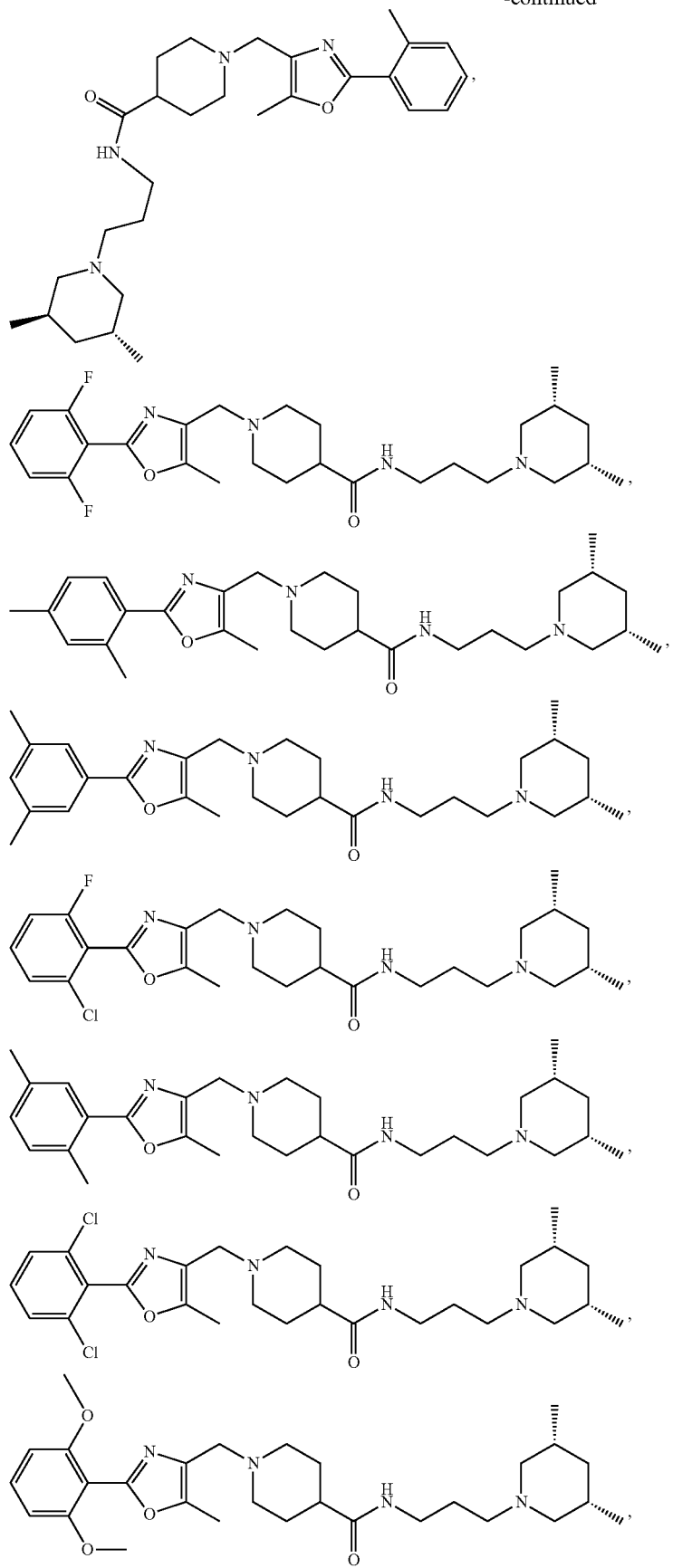

-continued
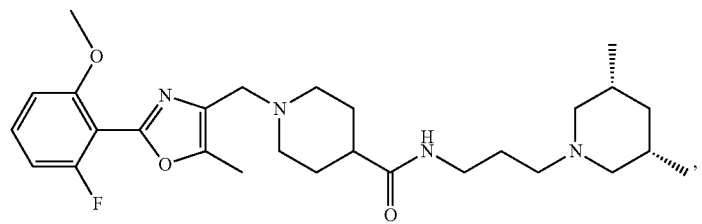
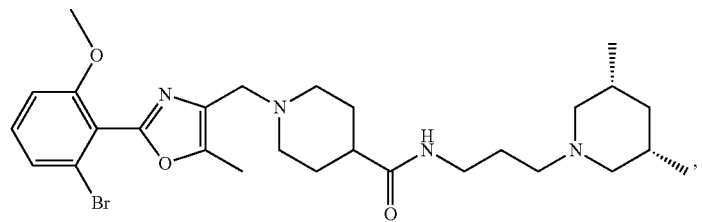
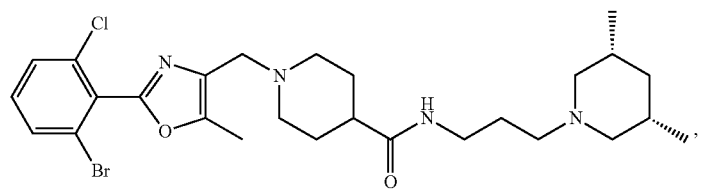
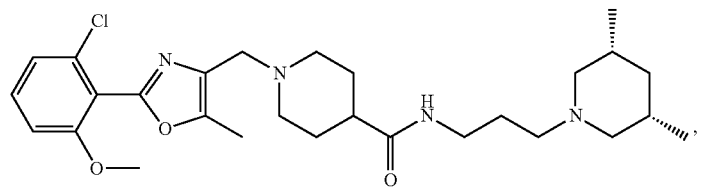
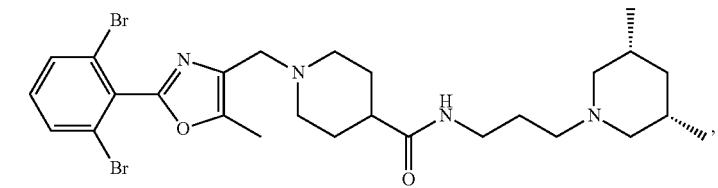
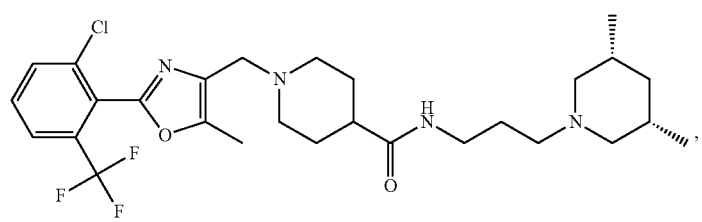
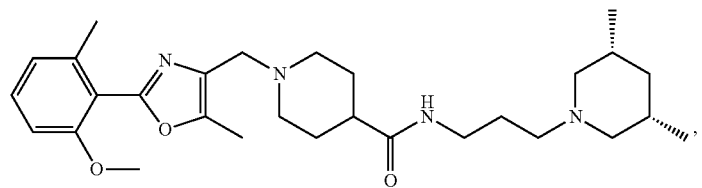
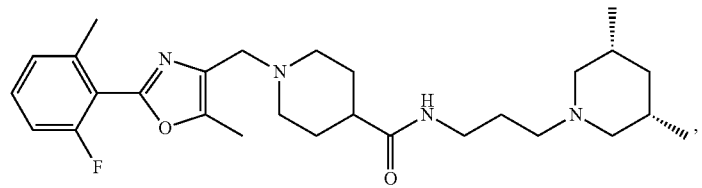

-continued
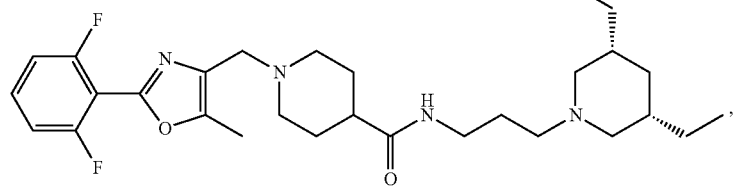
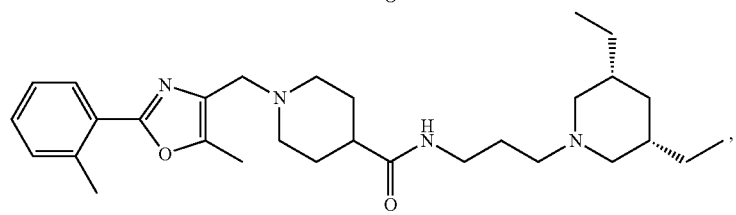
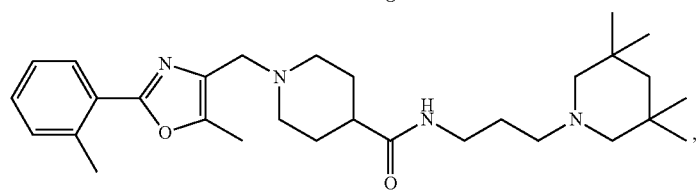
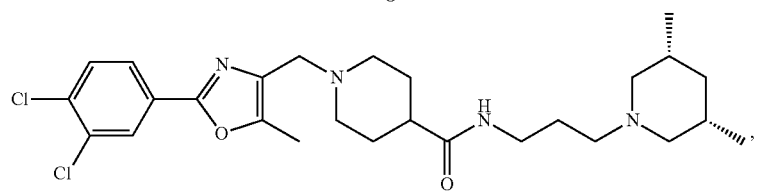
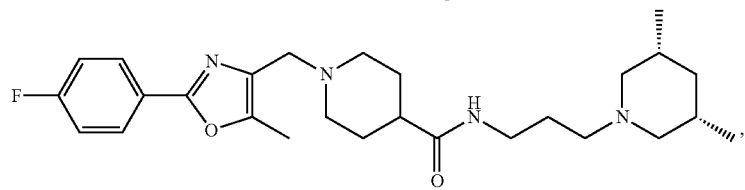
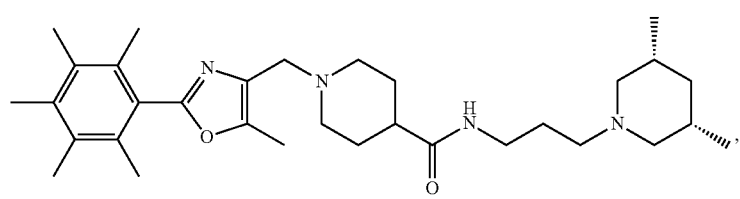
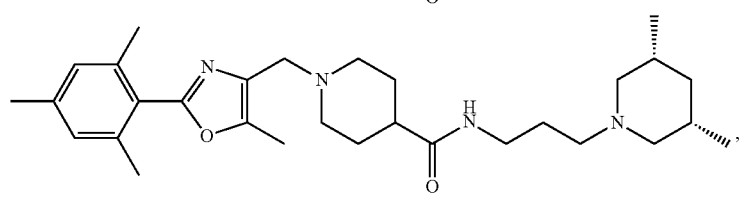
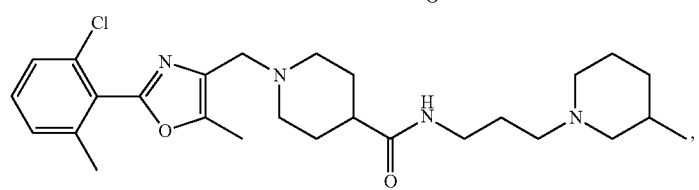
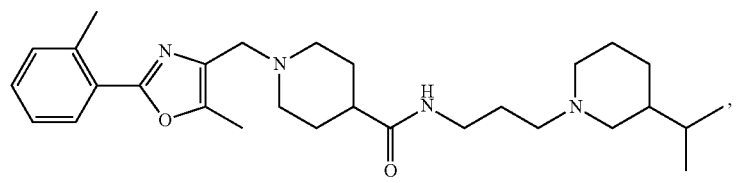

-continued
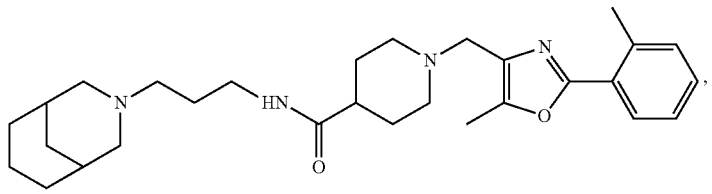
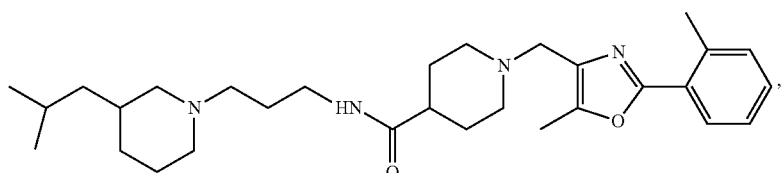
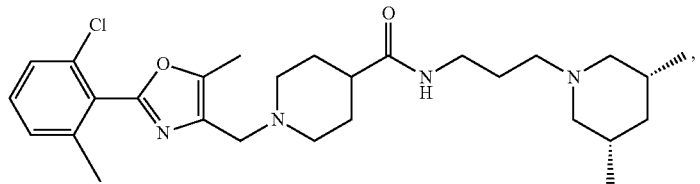
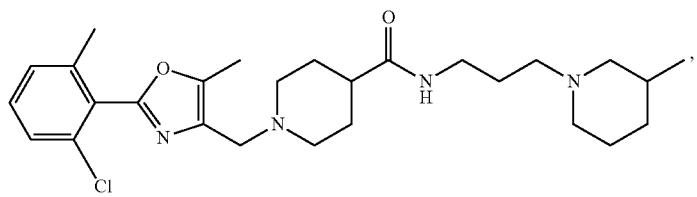
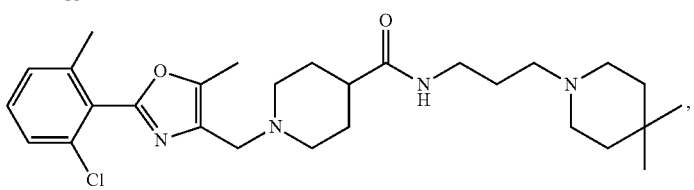
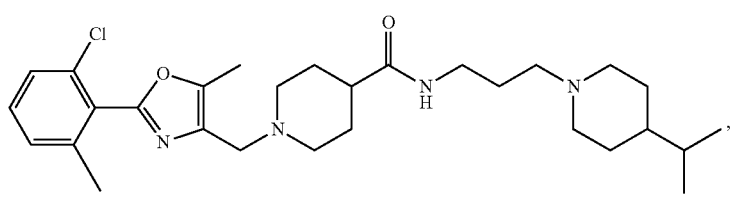
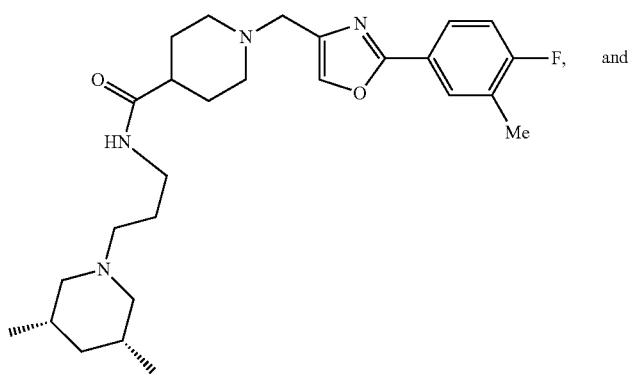 and 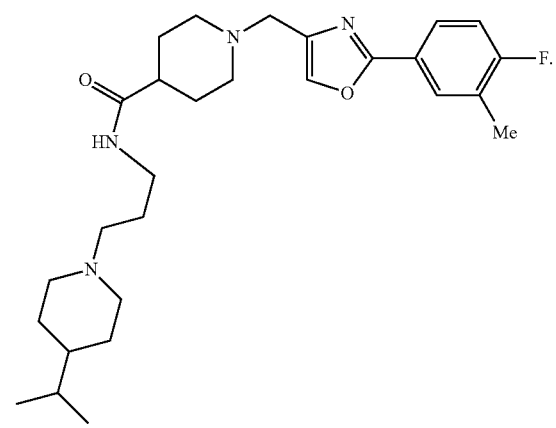

In certain more preferred embodiments, A is:

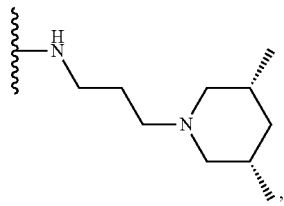

wherein the C-3 and C-5 carbon atoms bearing methyl groups on the piperidinyl ring of A have the absolute configuration: (3S, 5R).

In a particular preferred embodiment, the compound is:

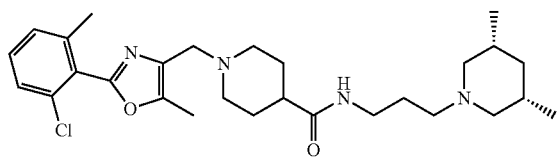

wherein the C-3 and C-5 carbon atoms bearing methyl groups on the piperidinyl ring of A have the absolute configuration: (3S, 5R).

In certain embodiments, Y is O.

In a particular embodiment, the compound is:

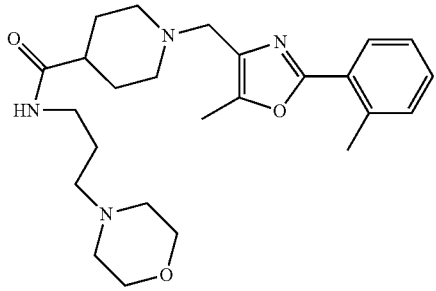 [SMILES: Cc1ccccc1-c1nc(CN2CCC(C(=O)NCCCN3CCOCC3)CC2)c(C)o1]

In certain embodiments, A is

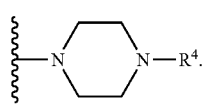

In certain preferred embodiments, $R^4$ is 1-methylpiperidin-4-yl or 2-(dimethylamino)ethyl.

In certain particular embodiments, the compound is:

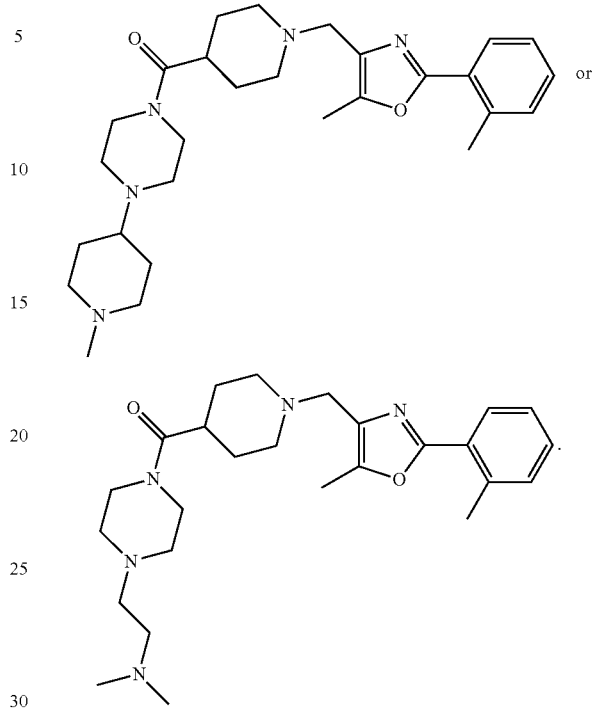

or

In certain embodiments, A is

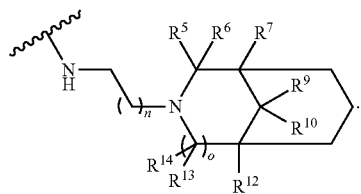

In certain preferred embodiments, A is

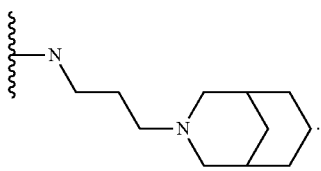 [SMILES: *NCCCN1CC2CCCC(C2)C1]

In a particular embodiment, the compound is:

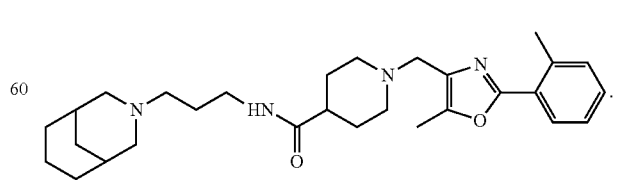

In certain embodiments, Ar is selected from naphth-1-yl, 2-methyl-naphth-1-yl, and anthracen-1-yl.

In certain particular embodiments, the compound is:

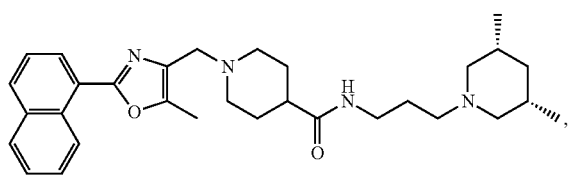

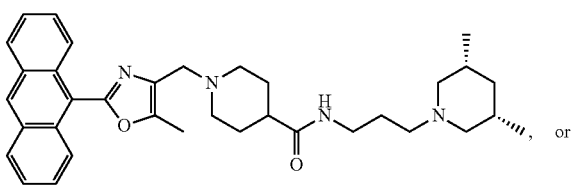, or

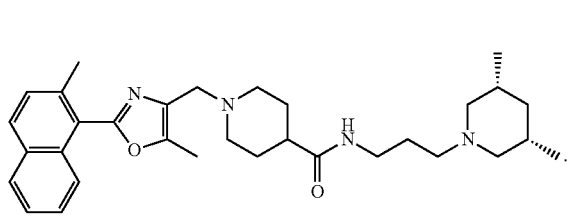

In certain embodiments, X is S.
In a particular embodiment, the compound is:

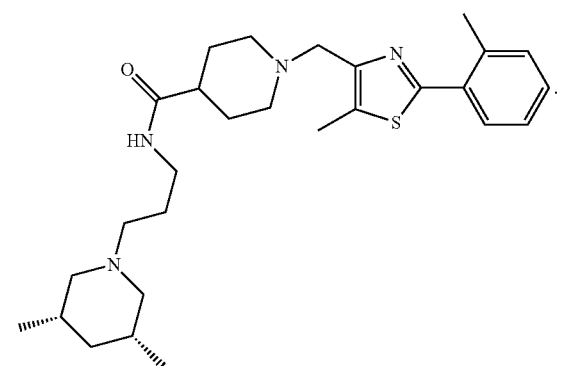 [SMILES: Cc1ccccc1-c1nc(CN2CCC(C(=O)NCCCN3C[C@H](C)C[C@H](C)C3)CC2)c(C)s1]

In certain embodiments, the compound is of formula (II).
In certain of these embodiments, A is

In a particular embodiment, the compound is:

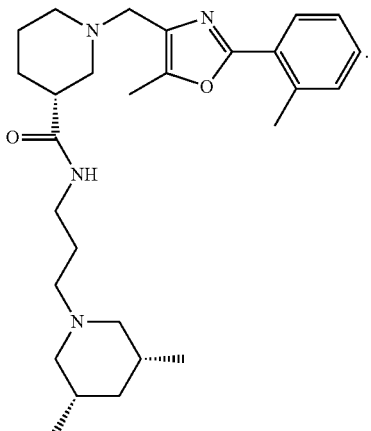 [SMILES: Cc1ccccc1-c1nc(CN2CCC[C@@H](C(=O)NCCCN3C[C@H](C)C[C@H](C)C3)C2)c(C)o1]

In certain embodiments, the compound is of formula (III):

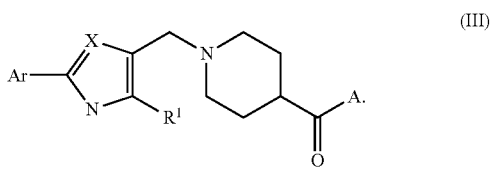

(III)

In certain of these embodiments, A is

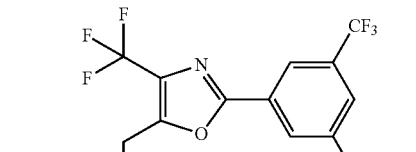

In a particular embodiment, the compound is:

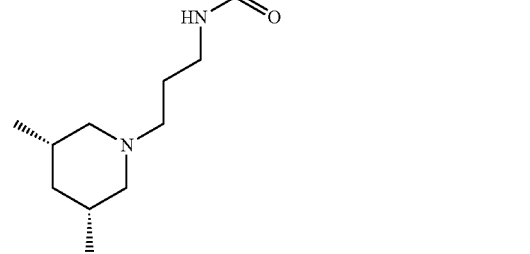 or

-continued

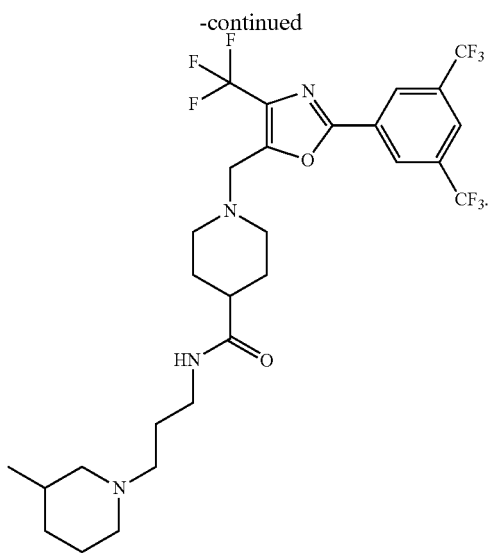

In an embodiment, the invention provides a compound or a pharmaceutically acceptable salt of formula (I) or formula (II) and a pharmaceutically acceptable carrier.

The phrase "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445, and *Journal of Pharmaceutical Science,* 66, 2-19 (1977).

Suitable bases include inorganic bases such as alkali and alkaline earth metal bases, e.g., those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. Preferred pharmaceutically acceptable salts of inventive compounds having an acidic moiety include sodium and potassium salts. Preferred pharmaceutically acceptable salts of inventive compounds having a basic moiety (e.g., a dimethylaminoalkyl group) include hydrochloride and hydrobromide salts. The compounds of the present invention containing an acidic or basic moiety are useful in the form of the free base or acid or in the form of a pharmaceutically acceptable salt thereof.

It should be recognized that the particular counterion forming a part of any salt of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

In any of the above embodiments, the compound or salt of formula (I), formula (II), or formula (III) can have at least one asymmetric carbon atom. When the compound or salt has at least one asymmetric carbon atom, the compound or salt can exist in the racemic form, in the form of its pure optical isomers, or in the form of a mixture wherein one isomer is enriched relative to the other. In particular, in accordance with the present invention, when the inventive compounds have a single asymmetric carbon atom, the inventive compounds may exist as racemates, i.e., as mixtures of equal amounts of optical isomers, i.e., equal amounts of two enantiomers, or in the form of a single enantiomer. As used herein, "single enantiomer" is intended to include a compound that comprises more than 50% of a single enantiomer (i.e., enantiomeric excess up to 100% pure enantiomer).

When the compound or salt has more than one chiral center, the compound or salt can therefore exist as a mixture of diastereomers or in the form of a single diastereomer. As used herein, "single diastereomer" is intended to mean a compound that comprises more than 50% of a single diastereomer (i.e., diastereomeric excess to 100% pure diastereomer).

The present invention further provides a pharmaceutical composition comprising a compound as described above and a pharmaceutically acceptable carrier. The present invention provides a pharmaceutical composition comprising a pharmaceutically acceptable carrier and an effective amount, e.g., a therapeutically effective amount, including a prophylactically effective amount, of one or more of the aforesaid compounds, or salts thereof, of the present invention.

The pharmaceutically acceptable carrier can be any of those conventionally used and is limited only by chemico-physical considerations, such as solubility and lack of reactivity with the compound, and by the route of administration. It will be appreciated by one of skill in the art that, in addition to the following described pharmaceutical compositions; the compounds of the present invention can be formulated as inclusion complexes, such as cyclodextrin inclusion complexes, or liposomes.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge foil is can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

In an embodiment, the invention provides a method of treating or preventing a viral infection in a mammal in need thereof comprising administering to the mammal an effective amount of a compound of formula (I), formula (II), or formula (III):

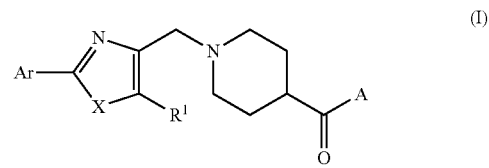

-continued

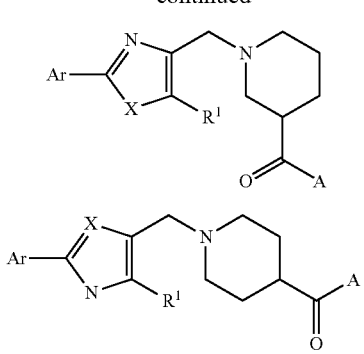

wherein Ar is optionally substituted $C_6$-$C_{14}$ aryl,
X is O or S,
$R^1$ is hydrogen, $C_1$-$C_6$ alkyl, or $CF_3$,
A is

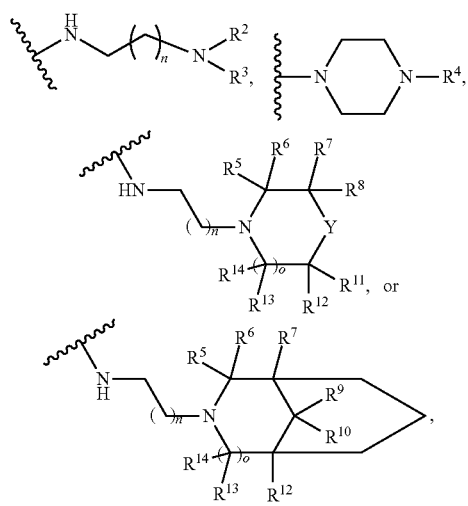

wherein n is an integer of 1 to 3,
o is 0 or 1,
Y is $CR^9R^{10}$ or O,
$R^2$ and $R^3$ are independently $C_1$-$C_6$ alkyl,
$R^4$ is di($C_1$-$C_6$ alkylamino)$C_2$-$C_6$ alkyl or a 5- or 6-membered N-containing heterocyclic ring, and
$R^5$-$R^{14}$ are independently hydrogen or $C_1$-$C_6$ alkyl,
or a pharmaceutically acceptable salt thereof, stereoisomer thereof, or mixture comprising stereoisomers thereof.

In these method embodiments, the compounds can be as recited for the compound embodiments of the invention.

In a preferred embodiment, the invention provides a method for treating or preventing hepatitis C.

In an embodiment, the inventive method further comprises administering to the mammal an effective amount of an anti-hepatitis C compound other than the compound of formula (I). Non-limiting examples of suitable anti-hepatitis C compounds include ribavirin, interferon-α, telaprevir, daclatasvir, cyclosporin A, sofosbuvir, asunaprevir (BMS-650032), boceprevir, GS-9451, GS-9256, ABT-450, danoprevir (RG7227), faldaprevir (BI 201335), IDX320, MK-5172, simeprevir (TMC435), sovaprevir (ACH-1625), ABT-267, ACH-3102, BMS-791325, daclatasvir (BMS-790052), GSK2336805, IDX719, JNJ-47910382, ledipasvir (GS-5885), MK-8742, PPI-461, PPI-668, ABT-333, ALS-002200, BI 207127, IDX184, INX-08189, mericitabine (RO5024048), PPI-383, PSI-352938, setrobuvir (ANA-598), sofosbuvir (PSI-7977 or GS-7977), tegobuvir (GS-9190), TMC647055, filibuvir (PF-00868554), GS-9669, GSK2878175, VX-135, VX-222, Algeron (cepeginterferon alfa-2b), BIP 48 (peginterferon alfa 2b 48 kDA), pegylated interferon alfa 2b, pegylated interferon lambda (BMS-914143), pegylated-P-Interferon-alpha-2b (P1101), alisporivir (DEB025), and IDX21437.

In an embodiment, the invention provides a method for synergistically enhancing the antiviral effect of an anti-hepatitis C compound in a mammal undergoing treatment with the anti-hepatitis C compound, which method comprises administering to the mammal a compound of the formula (I), formula (II), or formula (III). The compound of formula (I), formula (II), or formula (III) can be as described herein in connection with the method for treating or preventing hepatitis C.

In other embodiments, the inventive method is suitable for the treatment of a virus other than hepatitis C virus. For example, the inventive method is suitable for the treatment of a virus selected from Flaviviridae family of viruses such as West Nile virus, yellow fever virus, Japanese encephalitis virus, or dengue virus, and other families of viruses such as but not limiting to rhinovirus, polio virus, hepatitis A virus, hepatitis B virus, respiratory syncytial virus, severe acute respiratory syndrome (SARS), and Middle East respiratory syndrome coronavirus (MERS-CoV or MERS), and the like.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. Treatment of hepatitis C can be evidenced, for example, by a reduction in viral burden, a reduction in clinical symptoms resulting from the viral infection, or other parameters well known in the art that are specific to the viral infection, for example the hepatitis C infection. As used herein, the term "preventing," with reference to a disease or pathological condition, refers to blocking the appearance of a disease or a symptom associated with the disease, for example, the presence of a viral load, in an asymptomatic subject at risk of developing the disease, for example, by way of exposure to a virus.

By the term "coadminister" is meant that each of the at least two compounds be administered during a time frame wherein the respective periods of biological activity overlap. Thus, the term includes sequential as well as coextensive administration of two or more drug compounds. The compounds can be administered simultaneously, separately (chronologically staggered), cyclically, or sequentially and in any order, e.g., before or after.

The doses of the compound of formula (I) or formula (II) and/or the anti-hepatitis C compound administered to a mammal, particularly, a human, in accordance with the present invention should be sufficient to effect the desired response. Such responses include reversal or prevention of the adverse effects of the disease for which treatment is desired or to elicit the desired benefit. One skilled in the art will recognize that dosage will depend upon a variety of factors, including the age, condition, and body weight of the human, as well as the source, particular type of the disease, and extent of the disease in the human. The size of the doses will also be determined by the routes, timing and frequency of administration as well as the existence, nature, and extent of any adverse side-effects that might accompany the administration of a particular compound and the desired physiological effect. It will be appreciated by one of skill in the art that various conditions or disease states may require prolonged treatment involving multiple administrations.

Suitable doses and dosage regimens can be determined by conventional range-finding techniques known to those of ordinary skill in the art. Generally, treatment is initiated with smaller dosages that are less than the optimum dose of the compounds. Thereafter, the dosage is increased by small increments until the optimum effect under the circumstances is reached. The present inventive method typically will involve the administration of about 0.1 to about 300 mg of one or more of the compounds described above per kg body weight of the animal or mammal.

The therapeutically effective amount of the compound or compounds administered can vary depending upon the desired effects and the factors noted above. Typically, dosages will be between 0.01 mg/kg and 250 mg/kg of the subject's body weight, and more typically between about 0.05 mg/kg and 100 mg/kg, such as from about 0.2 to about 80 mg/kg, from about 5 to about 40 mg/kg or from about 10 to about 30 mg/kg of the subject's body weight. Thus, unit dosage forms can be formulated based upon the suitable ranges recited above and the subject's body weight. The term "unit dosage form" as used herein refers to a physically discrete unit of therapeutic agent appropriate for the subject to be treated.

Alternatively, dosages are calculated based on body surface area and from about 1 mg/m$^2$ to about 200 mg/m$^2$, such as from about 5 mg/m$^2$ to about 100 mg/m$^2$ will be administered to the subject per day. In particular embodiments, administration of the therapeutically effective amount of the compound or compounds involves administering to the subject from about 5 mg/m$^2$ to about 50 mg/m$^2$, such as from about 10 mg/m$^2$ to about 40 mg/m$^2$ per day. It is currently believed that a single dosage of the compounds is suitable, however a therapeutically effective dosage can be supplied over an extended period of time or in multiple doses per day. Thus, unit dosage forms also can be calculated using a subject's body surface area based on the suitable ranges recited above and the desired dosing schedule.

In accordance with an embodiment, the invention provides a method of treating cancer in a mammal in need thereof, comprising administering to the animal a compound of formula (I), formula (II), or formula (III) or pharmaceutically acceptable salts, stereoisomers, and mixtures comprising stereoisomers thereof. In accordance with these embodiments, the compound or salts, stereoisomers, and mixtures comprising stereoisomers thereof, of the invention is administered to the mammal by itself, i.e., without co-administration of an anticancer agent, radiation, or biotherapeutic agent. In some embodiments, the compound or salts, stereoisomers, and mixtures comprising stereoisomers thereof of the invention can be administered concomitantly with radiation and/or biotherapeutic agent.

The cancer can be any suitable cancer. For example, the cancer may be adrenocortical carcinoma, AIDS-related lymphoma, AIDS-related malignancies, anal cancer, cerebellar astrocytoma, extrahepatic bile duct cancer, bladder cancer, osteosarcoma/malignant fibrous histiocytoma, brain stem glioma, ependymoma, visual pathway and hypothalamic gliomas, breast cancer, bronchial adenomas/carcinoids, carcinoid tumors, gastrointestinal carcinoid tumors, carcinoma, adrenocortical, islet cell carcinoma, primary central nervous system lymphoma, cerebellar astrocytoma, cervical cancer, chronic lymphocytic leukemia, chronic myelogenous leukemia, clear cell sarcoma of tendon sheaths, colon cancer, colorectal cancer, cutaneous t-cell lymphoma, endometrial cancer, ependymoma, esophageal cancer, Ewing's sarcoma/family of tumors, extracranial germ cell tumors, extragonadal germ cell tumors, extrahepatic bile duct cancer, eye cancers, including intraocular melanoma, and retinoblastoma, gallbladder cancer, gastrointestinal carcinoid tumor, ovarian germ cell tumor, gestational trophoblastic tumor, hairy cell leukemia, head and neck cancer, Hodgkin's disease, hypopharyngeal cancer, hypothalamic and visual pathway glioma, intraocular melanoma, Kaposi's sarcoma, laryngeal cancer, acute lymphoblastic leukemia, acute myeloid leukemia, liver cancer, non-small cell lung cancer, small cell lung cancer, non-Hodgkin's lymphoma, Waldenstrom's macroglobulinemia, malignant mesothelioma, malignant thymoma, medulloblastoma, melanoma, intraocular melanoma, merkel cell carcinoma, metastatic squamous neck cancer with occult primary, multiple endocrine neoplasia syndrome, multiple myeloma/plasma cell neoplasm, mycosis fungoides, myelodysplastic syndrome, chronic myelogenous leukemia, myeloid leukemia, multiple myeloma, myeloproliferative disorders, nasal cavity and paranasal sinus cancer, nasopharyngeal cancer, neuroblastoma, oral cancer, oral cavity and lip cancer, oropharyngeal cancer, osteosarcoma/malignant fibrous histiocytoma of bone, ovarian cancer, ovarian low malignant potential tumor, pancreatic cancer, paranasal sinus and nasal cavity cancer, parathyroid cancer, penile cancer, pheochromocytoma, pituitary tumor, pleuropulmonary blastoma, prostate cancer, rectal cancer, renal cell (kidney) cancer, transitional cell cancer (e.g. renal pelvis and ureter), retinoblastoma, rhabdomyosarcoma, salivary gland cancer, malignant fibrous histiocytoma of bone, soft tissue sarcoma, sezary syndrome, skin cancer, small intestine cancer, stomach (gastric) cancer, supratentorial primitive neuroectodermal and pineal tumors, cutaneous t-cell lymphoma, testicular cancer, malignant thymoma, thyroid cancer, gestational trophoblastic tumor, urethral cancer, uterine sarcoma, vaginal cancer, vulvar cancer, and Wilms' tumor. In a preferred embodiment, the cancer is a non-small cell lung cancer.

In any of the embodiments of the invention, the cancer can be any cancer in any organ, for example, a cancer is selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof.

In an embodiment, the invention provides a pharmaceutical pack or kit comprising a compound of formula (I), formula (II), or formula (III) and an anti-hepatitis C compound other than a compound of formula (I), formula (II), or formula (III). The pharmaceutical pack or kit comprising one or more containers filled with a compound of formula (I), formula (II), or formula (III) and an anti-hepatitis C compound other than a compound of formula (I), formula (II), or formula (III). Optionally associated with such container(s) can be a notice in the form prescribed by a governmental agency regulating the manufacture, use or sale of pharmaceuticals or biological products, which notice reflects approval by the agency of manufacture, use or sale for human administration.

The following examples further illustrate the invention but, of course, should not be construed as in any way limiting its scope.

General Chemistry Methods. All reagents were used as received from the following suppliers: Alfa Aesar, Ark Pharm, Aldrich, and Fisher Scientific. Acetonitrile and THF were purified using the Innovative Technology PureSolv solvent purification system. The $^1$H and $^{13}$C spectra were recorded on a Bruker Avance 400 MHz or 500 MHz spectrometer. Chemical shifts are reported in parts per million and were referenced to residual proton solvent signals. Flash column chromatography separations were performed using the Teledyne Isco CombiFlash RF using RediSep RF silica gel columns. TLC was performed on Analtech UNIPLATE silica gel GHLF plates (gypsum inorganic hard layer with fluorescence). TLC plates were developed using iodine vapor. Automated preparative RP HPLC purification was performed using an Agilent 1200 Mass-Directed Fractionation system (Prep Pump G1361 with gradient extension, make-up pump G1311 A, pH modification pump G1311A, HTS PAL autosampler, UV-DAD detection G1315D, fraction collector G1364B, and Agilent 6120 quadrapole spectrometer G6120A). The preparative chromatography conditions included a Waters X-Bridge C18 column (19°—150 mm, 5 μn, with 19°—10-mm guard column), elution with a water and acetonitrile gradient, which increases 20% in acetonitrile content over 4 min at a flow rate of 20 mL/min (modified to pH 9.8 through addition of NH4OH by auxiliary pump), and sample dilution in DMSO. The preparative gradient, triggering thresholds, and UV wavelength were selected according to the analytical RP HPLC analysis of each crude sample. The analytical method used an Agilent 1200 RRLC system with UV detection (Agilent 1200 DAD SL) and mass detection (Agilent 6224 TOF). The analytical method conditions included a Waters Aquity BEH C18 column (2.1°—50 mm, 1.7 μm) and elution with a linear gradient of 5% acetonitrile in pH 9.8 buffered aqueous ammonium formate to 100% acetonitrile at 0.4 mL/min flow rate. Compound purity was measured on the basis of peak integration (area under the curve) from UV/vis absorbance (at 214 nm), and compound identity was determined on the basis of mass analysis. All compounds used for biological studies have purity >90%.

Example 1

This example demonstrates a method of synthesis of a compound in accordance with an embodiment of the invention.

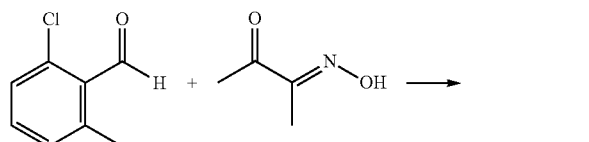

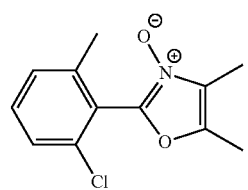

2-(2-Chloro-6-methylphenyl)-4,5-dimethyloxazole 3-oxide. To a mixture of (E)-3-(hydroxyimino)butan-2-one (0.417 g, 4.13 mmol) and 2-chloro-6-methylbenzaldehyde (0.702 g, 4.54 mmol) in acetic acid (25.0 mL) at 0° C., was added HCl (1.55 mL, 4.0 M, 6.19 mmol). The reaction mixture was allowed to warm to room temperature and stirred for 16 h, diluted with MTBE and filtered. The solid was collected, washed with ethyl ether and dried to afford the product as a tan solid, which was used without further purification (0.797 g, 3.35 mmol, 81% yield). 1H NMR (400 MHz, CDCl3) δ 7.52 (t, J=8.0 Hz, 1H), 7.39 (d, J=8.0 Hz, 1H), 7.29 (d, J=8.0 Hz, 1H), 2.53 (s, 6H), 2.42 (s, 3H). 13C NMR (101 MHz, CDCl3) δ 153.8, 147.5, 143.0, 134.5, 129.3, 127.3, 118.9, 20.4, 11.2, 7.4. HRMS (m/z): calcd for C12H13ClNO2 ([M]++H) 238.0635; found 238.0627; HPLC purity: 95.1%.

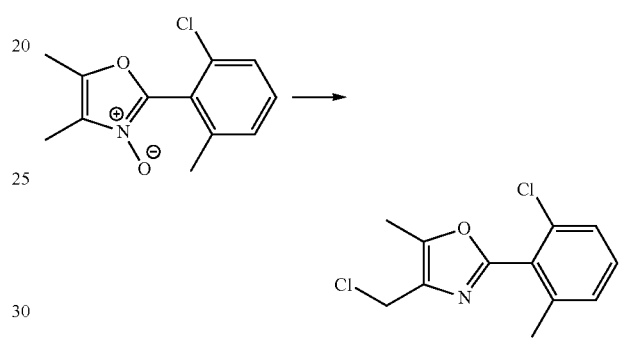

2-(2-Chloro-6-methylphenyl)-4-(chloromethyl)-5-methyloxazole. To a solution of 2-(2-chloro-6-methylphenyl)-4,5-dimethyloxazole-3-oxide (789 mg, 3.32 mmol) in DCE (20.0 mL), was added POCl3 (0.340 mL, 3.65 mmol). The reaction was heated at reflux for 30 min, then cooled to rt, carefully quenched with water and extracted with DCM (2×20.0 mL). The evaporated residue was purified via silica gel chromatography with EtOAc/hexanes to give a colorless oil (327 mg, 1.28 mmol, 39% yield). 1H NMR (400 MHz, CDCl3) δ 7.33-7.21 (m, 2H), 7.21-7.11 (m, 1H), 4.58 (s, 2H), 2.42 (s, 3H), 2.26 (s, 3H); 13C NMR (101 MHz, CDCl3) δ 156.9, 147.0, 141.0, 134.7, 132.2, 131.0, 128.5, 127.6, 127.0, 37.2, 20.3, 10.3; HRMS (m/z): calcd. for C12H12Cl2NO ([M]++H) 256.0296; found 256.0288; HPLC purity: 98.1%.

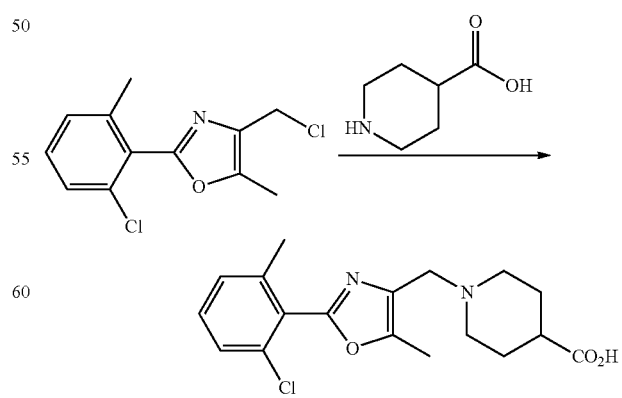

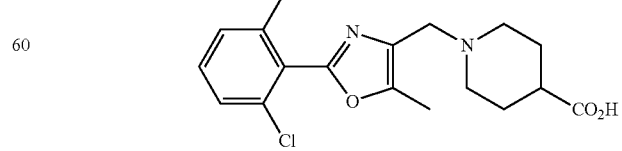

1-((2-(2-Chloro-6-methylphenyl)-5-methyloxazol-4-yl)methyl)piperidine-4-carboxylic acid. To a solution of piperidine-4-carboxylic acid (98.0 mg, 0.759 mmol) and potassium hydroxide (85 mg, 1.52 mmol) in ethanol (5.0 mL), was added 2-(2-chloro-6-methylphenyl)-4-(chloromethyl)-5-methyloxazole (130 mg, 0.506 mmol) in EtOH (2.0 mL). The mixture was stirred at rt for 16 h. Solvent was removed in vacuo and the residue was purified via C-18 silica gel chromatography with MeCN/water to give a colorless oil (113 mg, 0.323 mmol, 64% yield). 1H NMR (400 MHz, DMSO-d6) δ 7.50-7.40 (m, 2H), 7.40-7.31 (m, 1H), 3.42 (s, 2H), 2.82-2.78 (m, 2H), 2.36 (s, 3H), 2.19 (s, 3H), 2.05-1.98 (m, 3H), 1.80-1.69 (m, 2H), 1.56-1.46 (m, 2H); 13C NMR (126 MHz, DMSO-d6) δ 176.8, 155.0, 146.4, 140.7, 133.4, 131.5, 131.4, 128.9, 127.7, 126.9, 52.7, 52.3, 41.5, 28.6, 19.7, 9.9; HRMS (m/z): calcd. for C18H22ClN2O3 ([M]++H) 349.1319; found 349.1340; HPLC purity: 97.8%.

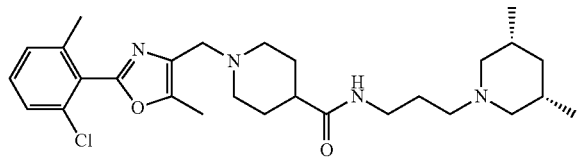 [SMILES: Cc1cccc(Cl)c1-c1nc(CN2CCC(C(=O)NCCCN3C[C@H](C)C[C@H](C)C3)CC2)c(C)o1]

1-((2-(2-Chloro-6-methylphenyl)-5-methyloxazol-4-yl)methyl)-N-(3-(cis-3,5-dimethylpiperidin-1-yl)propyl)piperidine-4-carboxamide (ML391). A mixture of 1-((2-(2-chloro-6-methylphenyl)-5-methyloxazol-4-yl)methyppiperidine-4-carboxylic acid (80.0 mg, 0.229 mmol), 3-((3S,5R)-3,5-dimethylpiperidin-1-yl)propan-1-amine (58.6 mg, 0.344 mmol), HOBT (35.1 mg, 0.229 mmol), DIC (0.071 mL, 0.459 mmol) and DMAP (1.4 mg, 0.011 mmol) in MeCN (2.5 mL) was heated under microwave irradiation at 100° C. for 10 min. Solvent was removed and the residue was purified via silica gel chromatography with DCM/(MeOH containing 1% Et3N). The resulting oil was further purified through preparative reverse phase HPLC to give a colorless oil (70.8 mg, 0.141 mmol, 62% yield). 1H NMR (400 MHz, CDCl3) δ 7.36 (t, J=4.6 Hz, 1H), 7.31-7.23 (m, 2H), 7.19-7.12 (m, 1H), 3.53 (s, 2H), 3.37-3.28 (m, 2H), 3.04-2.99 (m, 2H), 2.88-2.84 (m, 2H), 2.40 (t, J=9.1 Hz, 2H), 2.39 (s, 3H), 2.24 (s, 3H), 2.14-2.07 (m, 2H), 2.04-1.96 (m, 1H), 1.89-1.53 (m, 9H), 1.39 (t, J=11.0 Hz, 2H), 0.86 (d, J=6.5 Hz, 6H), 0.53 (q, J=12.0 Hz, 1H); 13C NMR (101 MHz, CDCl3) δ 174.7, 156.1, 146.4, 140.8, 134.8, 131.6, 130.6, 128.3, 128.2, 126.8, 61.8, 58.3, 53.4, 52.8, 43.4, 42.1, 40.0, 31.3, 29.0, 24.8, 20.2, 19.6, 10.3; HRMS (m/z): calcd. for C28H42ClN4O2 ([M]++H) 501.2996; found 501.2995; HPLC purity: 96.1%.

Example 2

This example provides characterization data for compounds in accordance with an embodiment of the invention.

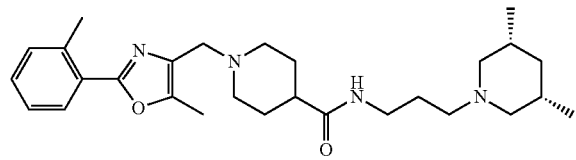 [SMILES: Cc1ccccc1-c1nc(CN2CCC(C(=O)NCCCN3C[C@H](C)C[C@H](C)C3)CC2)c(C)o1]

N-(3-((3S,5R)-3,5-Dimethylpiperidin-1-yl)propyl)-1-((5-methyl-2-(o-tolypoxazol-4-yl)methyl)piperidine-4-carboxamide. Yield: 51.4 mg, 69%. 1H NMR (400 MHz, CDCl3) δ 7.96-7.93 (m, 1H), 7.39-7.32 (m, 1H), 7.32-7.22 (m, 3H), 3.50 (s, 2H), 3.37-3.32 (m, 2H), 3.07-3.03 (m, 2H), 2.95-2.86 (m, 2H), 2.66 (s, 3H), 2.45 (t, J=6.2 Hz, 2H), 2.40 (s, 3H), 2.17-1.97 (m, 3H), 1.91-1.64 (m, 9H), 1.44 (t, J=11.0 Hz, 2H), 0.88 (d, J=6.5 Hz, 6H), 0.63-0.49 (m, 1H). 13C NMR (101 MHz, CDCl3) δ 174.9, 159.7, 145.5, 137.0, 132.3, 131.4, 129.4, 128.7, 126.9, 125.8, 61.6, 58.1, 53.9, 53.08, 43.4, 42.0, 39.8, 31.2, 29.0, 24.8, 21.8, 19.6, 10.5. HRMS (m/z): calcd. for C28H43N4O2 ([M]++H) 467.3386; found 467.3392; HPLC purity: 100%.

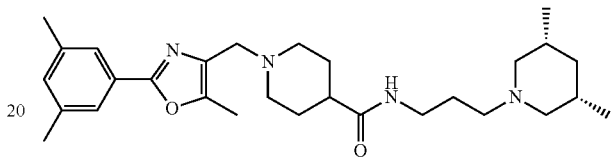

1-((2-(3,5-Dimethylphenyl)-5-methyloxazol-4-yl)methyl)-N-(3-((3S,5R)-3,5-dimethylpiperidin-1-yl)propyl)piperidine-4-carboxamide. Yield: 46.7 mg, 64%. 1H NMR (400 MHz, CDCl3) δ 7.66 (s, 2H), 7.32 (t, J=4.6 Hz, 1H), 7.05 (s, 1H), 3.45 (s, 2H), 3.39-3.29 (m, 2H), 3.04-3.00 (m, 2H), 2.91-2.87 (m, 2H), 2.43 (t, J=6.1 Hz, 2H), 2.39 (s, 3H), 2.36 (s, 6H), 2.12-1.97 (m, 3H), 1.88-1.61 (m, 9H), 1.43 (t, J=11.0 Hz, 2H), 0.88 (d, J=6.5 Hz, 6H), 0.56 (q, J=11.9 Hz, 1H). 13C NMR (101 MHz, CDCl3) δ 174.9, 159.7, 145.8, 138.2, 132.6, 131.5, 127.5, 123.8, 61.7, 58.2, 54.0, 53.2, 43.4, 42.0, 39.8, 31.3, 29.0, 24.8, 21.2, 19.6, 10.4. HRMS (m/z): calcd. for C29H45N4O2 ([M]++H) 481.3543; found 481.3547; HPLC purity: 100%.

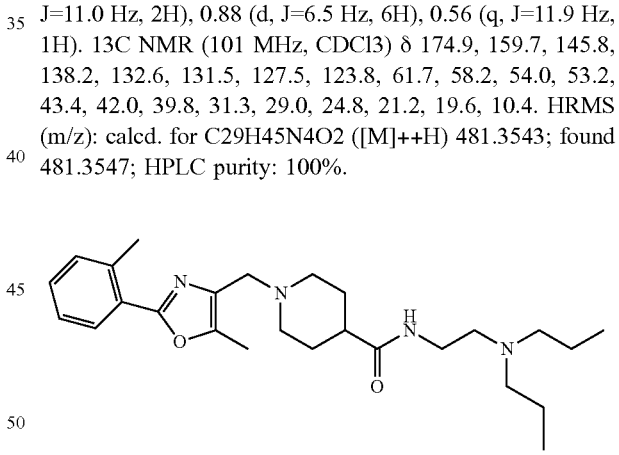

N-(2-(Dipropylamino)ethyl)-1-((5-methyl-2-(o-tolypoxazol-4-yl)methyppiperidine-4-carboxamide. Yield: 20.3 mg, 29%. 1H NMR (400 MHz, CDCl3) δ 7.96-7.94 (m, 1H), 7.35-7.21 (m, 3H), 3.53 (s, 2H), 3.46-3.38 (m, 2H), 3.34-3.20 (m, 2H), 3.10-3.04 (m, 2H), 2.77 (q, J=6.8 Hz, 2H), 2.67 (s, 3H), 2.64-2.56 (m, 2H), 2.41 (s, 3H), 2.18 Page 28 of 31-2.10 (m, 2H), 2.04-1.87 (m, 2H), 1.72-1.42 (m, 7H), 0.98-0.84 (m, 6H). 13C NMR (101 MHz, CDCl3) δ 175.4, 175.3, 159.7, 145.6, 137.0, 132.3, 131.4, 129.4, 128.6, 126.9, 125.8, 53.9, 53.0, 52.9, 52.0, 51.8, 50.0, 48.7, 47.68, 47.66, 47.6, 46.2, 38.9, 38.8, 29.0, 23.3, 23.2, 22.9, 21.9, 21.0, 11.74, 11.72, 11.3, 11.2, 10.5. HRMS (m/z): calcd. for C26H41N4O2 ([M]++H) 441.3230; found 441.3227; HPLC purity: 100%.

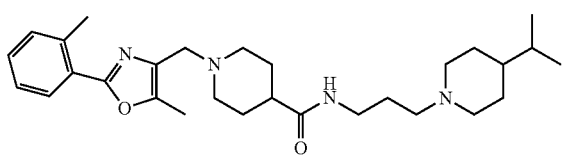 [SMILES: Cc1ccccc1-c1nc(CN2CCC(C(=O)NCCCN3CCC(C(C)C)CC3)CC2)c(C)o1]

N-(3-(4-Isopropylpiperidin-1-yl)propyl)-1-((5-methyl-2-(o-tolyl)oxazol-4-yl)methyl)piperidine-4-carboxamide.
Yield: 55.0 mg, 55%. 1H NMR (400 MHz, CDCl3) δ 7.92 (dd, J=8.0, 1.7 Hz, 1H), 7.59 (t, J=4.6 Hz, 1H), 7.33-7.17 (m, 3H), 3.47 (s, 2H), 3.34-3.30 (m, 2H), 3.08-2.92 (m, 4H), 2.65 (s, 3H), 2.45-2.39 (m, 2H), 2.38 (s, 3H), 2.14-1.96 (m, 3H), 1.91-1.73 (m, 6H), 1.67-1.61 (m, 4H), 1.40 (dq, J=13.3, 6.4 Hz, 1H), 1.33-1.15 (m, 2H), 1.08-0.99 (m, 1H), 0.83 (d, J=6.8 Hz, 6H). 13C NMR (101 MHz, CDCl3) δ 174.8, 174.7, 159.7, 145.6, 137.0, 132.3, 131.4, 129.4, 128.7, 126.9, 125.8, 58.5, 54.5, 53.8, 53.1, 43.4, 42.2, 40.2, 32.4, 29.4, 29.1, 24.7, 21.8, 19.6, 10.4. HRMS (m/z): calcd. for C29H45N4O2 ([M]++H) 481.3543; found 481.3537; HPLC purity: 100%.

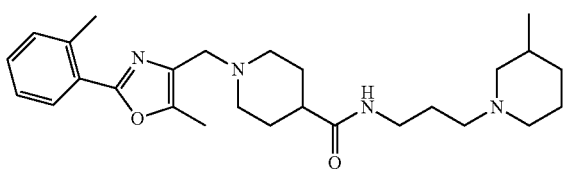 [SMILES: Cc1ccccc1-c1nc(CN2CCC(C(=O)NCCCN3CCCC(C)C3)CC2)c(C)o1]

1-((5-Methyl-2-(o-tolyl)oxazol-4-yl)methyl)-N-(3-(3-methylpiperidin-1-yl)propyl)piperidine-4-carboxamide.
Yield: 49.0 mg, 68%. 1H NMR (400 MHz, CDCl3) δ 7.94 (dd, J=8.1, 1.7 Hz, 1H), 7.38 (t, J=4.7 Hz, 1H), 7.35-7.21 (m, 3H), 3.50 (s, 2H), 3.35 (q, J=5.8 Hz, 2H), 3.08-3.03 (m, 2H), 2.95-2.83 (m, 2H), 2.66 (s, 3H), 2.43 (t, J=6.1 Hz, 2H), 2.40 (s, 3H), 2.17-1.98 (m, 3H), 1.90-1.61 (m, 10H), 1.58-1.50 (m, 2H), 0.97-0.82 (m, 4H). 13C NMR (101 MHz, CDCl3) δ 174.9, 159.7, 145.5, 137.0, 132.4, 131.4, 129.4, 128.7, 126.9, 125.8, 62.2, 58.4, 54.1, 53.9, 53.1, 43.5, 39.9, 32.9, 31.3, 29.09, 29.05, 25.6, 24.7, 21.8, 19.7, 10.5. HRMS (m/z): calcd. for C27H41N4O2 ([M]++H) 453.3230; found 453.3228; HPLC purity: 100%.

Example 3

This example demonstrates the determination of aqueous solubility for a compound in accordance with an embodiment of the invention.

Aqueous solubility was measured in phosphate buffered saline (PBS) at room temperature (23° C.). PBS by definition is 137 mM NaCl, 2.7 mM KCl, 10 mM sodium phosphate dibasic, 2 mM potassium phosphate monobasic and a pH of 7.4. The solubility of compound 1 was determined to be >74 μg/mL (>147 μM) at pH 7.4.

Example 4

This example demonstrates the stability of compound 1 in accordance with an embodiment of the invention.

Procedure: Compound was dissolved at 10 μM in PBS or PBS/acetonitrile (1/1) at pH 7.4 (1% DMSO) and incubated at room temperature with either no thiol source as a negative control or 50 μM dithiothreitol (DTT). The mixtures were sampled every hour for eight hours or every 8 hours for 48 hours and analyzed by RP HPLC/UV/HRMS. The analytical RP HPLC/UV/HRMS system utilized for the analysis was a Waters Acquity system with UV-detection and mass-detection (Waters SQD). The analytical method conditions included a Waters Acquity HSS Atlantis C18 column (2.1× 50 mm, 1.8 μm) and elution with a linear gradient of 99% water to 100% CH3CN at 0.6 mL/min flow rate. Peaks on the 214 nm chromatographs were integrated using the Waters OpenLynx software. Absolute areas under the curve were compared at each time point to determine relative percent compound remaining. The masses of potential adducts were searched for in the final samples to determine if any detectable adduct formed. All samples were prepared in duplicate and the average plotted. Ethacrynic acid, a known Michael acceptor, was used as a positive control. The compound 1 was found to be stable and soluble at 10 μM over the 48 hour test period in both PBS buffer (FIG. 1A) and PBS buffer with 50% (v/v) acetonitrile solvent systems (FIG. 1B). After 48 hours of sampling, greater than 97% of the sample was still detected in the supernatant. To determine the stability of the probe compound to nucleophilic degradation, the compound was dissolved in the two solvent systems above in the presence of 50 μM dithiothreitol (DTT) (FIGS. 2A and 2B). After 8 hours, no measurable degradation had occurred in either solvent system, indicating that 1 possessed robust resistance to nucleophilic attack.

Example 5

This example demonstrates the dose response curves for compound 1 in accordance with an embodiment of the invention.

HCVcc harboring a luciferase reporter gene (HCVcc-RLuc, genotype 2a) was used to infect Huh7.5.1 cells in the presence of increasing concentrations of tested compound 1. Viral infection and replication were measured by luciferase signal 48 h after treatment. Cytotoxicity was evaluated in parallel with the ATP-based cell viability assay (ATPlite). The results are the mean from three replicates±SEM. The $EC_{50}$ and $CC_{50}$ values were calculated with GraphPad Prism 5.0 software using nonlinear regression. The results are illustrated in FIG. 3, with the $EC_{50}$ curve shown by triangles and $CC_{50}$ curve shown by circles.

Example 6

This example demonstrates the $EC_{50}$ and $CC_{50}$ values against HCV according to the HCVcc-RLuc reporter assay described in Example 5 and the cytotoxicity using the Huh 7.5.1 ATPlite assay for compounds in accordance with an embodiment of the invention. The results are set forth in Table 1. Table 1 further contains data on the rat liver microsome assay, cell permeability, and solubility.

TABLE 1

| | Ar | A | EC$_{50}$ | CC$_{50}$ | Rat liver microsomes t ½ (min) | Permeability (1e$^{-6}$ cm/s) | Sol. (µg/mL) |
|---|---|---|---|---|---|---|---|
| 1 | 2-chloro-6-methylphenyl | (3,5-dimethylpiperidin-1-yl)propylamino | 0.014 | 14.1 | 2.9 | 196.3 | >74.0 |
| 2 | 2-methylphenyl | N-methyl-N'-dipropyl ethylenediamine | 0.18 | 30.9 | >30.0 | 913.1 | >65.0 |
| 3 | 2-methylphenyl | (3,5-dimethylpiperidin-1-yl)propylamino | 0.126 | 13.4 | >30.0 | 489.1 | 53.9 |
| 4 | 3,5-dimethylphenyl | (3,5-dimethylpiperidin-1-yl)propylamino | 0.036 | 4.11 | <30.0 | 864 | >71.0 |
| 5 | 2-methylphenyl | (4-isopropylpiperidin-1-yl)propylamino | 0.054 | 4.28 | 8.8 | 395.8 | >71.0 |
| 6 | 2-methylphenyl | (3-methylpiperidin-1-yl)propylamino | 0.042 | 15 | >30.0 | ND | >67.0 |
| 7 | 3,5-dimethoxyphenyl | N-methyl-(3,5-dimethylpiperidin-1-yl)propylamino | 0.68 | 58.7 | >30.0 | 81.9 | >76.0 |

TABLE 1-continued

| | Ar | A | EC$_{50}$ | CC$_{50}$ | Rat liver microsomes t ½ (min) | Permeability (1e$^{-6}$ cm/s) | Sol. (μg/mL) |
|---|---|---|---|---|---|---|---|
| 8 | 3,5-diMeO-phenyl | —NH-(CH$_2$)$_4$-N(Et)$_2$ | 6.55 | >100 | >30.0 | 10.4 | >72.0 |
| 9 | o-tolyl | —NH-(CH$_2$)$_3$-piperidinyl | 0.82 | 18.1 | >30.0 | 34.5 | >65.0 |
| 10 | o-tolyl | —NH-(CH$_2$)$_3$-(4-methylpiperidinyl) | 0.4 | 12.6 | >30.0 | 424.7 | >67.0 |
| 11 | o-tolyl | —NH-(CH$_2$)$_2$-piperidinyl | 1.2 | 23 | >30.0 | 987.3 | 47 |
| 12 | o-tolyl | —NH-(CH$_2$)$_3$-morpholinyl | 1.9 | 64.3 | >30.0 | 432.4 | >65.0 |
| 13 | o-tolyl | 4-(4-methylpiperidin-1-yl)piperazin-1-yl | 3.2 | 20 | >30.0 | <3.2 | >71.0 |
| 14 | o-tolyl | 4-(2-(dimethylamino)ethyl)piperazin-1-yl | 6.1 | 27.4 | >30.0 | 14 | >67.0 |
| 15 | o-Cl-phenyl | —NH-(CH$_2$)$_3$-(3,5-dimethylpiperidinyl) | 0.086 | 16.2 | 15 | 352.4 | >72.0 |

TABLE 1-continued

| | Ar | A | EC$_{50}$ | CC$_{50}$ | Rat liver microsomes t ½ (min) | Permeability (1e$^{-6}$ cm/s) | Sol. (μg/mL) |
|---|---|---|---|---|---|---|---|
| 16 | 4-Cl-phenyl | 3,5-dimethylpiperidinyl-propylamine | 0.11 | 6.2 | >30.0 | >635.0 | >72.0 |
| 17 | 2-ethylphenyl | 3,5-dimethylpiperidinyl-propylamine | 0.14 | 9.59 | 17 | 106.1 | 55.9 |
| 18 | 3-methylphenyl | 3,5-dimethylpiperidinyl-propylamine | 0.12 | 13 | >30.0 | 279.1 | >69.0 |
| 19 | 4-methylphenyl | 3,5-dimethylpiperidinyl-propylamine | 0.1 | 6.2 | >30.0 | 274.3 | >69.0 |
| 20 | 2-methylphenyl | 3,5-dimethylpiperidinyl-ethylamine | 0.17 | 24.6 | >30.0 | 712.4 | >67.0 |
| 21 | 2-methylphenyl | 3,5-dimethylpiperidinyl-butylamine | 0.17 | 23.1 | 12 | 287.8 | >71.0 |
| 22 | 3,4-dimethylphenyl | 3,5-dimethylpiperidinyl-propylamine | 0.098 | 6.2 | >30.0 | 219.4 | >71.0 |

TABLE 1-continued

[Structure: Ar—oxazole(N,O with 5-methyl)—CH₂—N-piperidine-4-C(=O)—A]

| | Ar | A | EC$_{50}$ | CC$_{50}$ | Rat liver microsomes t ½ (min) | Permeability (1e$^{-6}$ cm/s) | Sol. (μg/mL) |
|---|---|---|---|---|---|---|---|
| 23 | 2,3-dimethylphenyl | NH-propyl-(3,5-dimethylpiperidine) | 0.051 | 20.5 | 3.1 | 253.9 | 55.9 |
| 24 | 3-chlorophenyl | NH-propyl-(3,5-dimethylpiperidine) | 0.12 | 4.2 | >30.0 | 615.1 | >72.0 |
| 25 | 2-methylphenyl | NH-propyl-(3,5-dimethylpiperidine) | 0.034 | 10.2 | >30.0 | 241.4 | >69.0 |
| 26 | 2-methylphenyl | NH-propyl-(3,5-dimethylpiperidine) | 0.059 | 9.4 | 14 | 553.7 | >69.0 |
| 27 | 2-methylphenyl | NH-propyl-(3,5-dimethylpiperidine) | 0.144 | 21.3 | >30.0 | 55.4 | >69.0 |
| 28 | 2-methylphenyl | NH-propyl-(3,5-dimethylpiperidine) (+) isomer | 0.074 | 14.2 | 7.6 | 497.7 | 54.8 |

TABLE 1-continued

| | Ar | A | EC$_{50}$ | CC$_{50}$ | Rat liver microsomes t ½ (min) | Permeability (1e$^{-6}$ cm/s) | Sol. (μg/mL) |
|---|---|---|---|---|---|---|---|
| 29 | o-tolyl | (−)-isomer: N-propyl-(3,5-dimethylpiperidinyl) | 0.125 | 14 | 7.3 | ND | >69.0 |
| 30 | 2,6-difluorophenyl | N-propyl-(3,5-dimethylpiperidinyl) | 0.624 | >31.6 | 21 | 82.7 | >72.0 |
| 31 | 1-naphthyl | N-propyl-(3,5-dimethylpiperidinyl) | 0.063 | 4.16 | >30.0 | ND | >74.0 |
| 32 | 2,4-dimethylphenyl | N-propyl-(3,5-dimethylpiperidinyl) | 0.084 | 4.11 | >30.0 | 353.1 | >71.0 |
| 33 | 2-fluoro-6-chlorophenyl | N-propyl-(3,5-dimethylpiperidinyl) | 0.334 | 13.3 | 4 | ND | >75.0 |
| 34 | 2,5-dimethylphenyl | N-propyl-(3,5-dimethylpiperidinyl) | 0.093 | 4.09 | 30 | ND | 56.1 |
| 35 | 2,6-dichlorophenyl | N-propyl-(3,5-dimethylpiperidinyl) | 0.221 | 13.2 | 2.9 | ND | >77.0 |

TABLE 1-continued

| | Ar | A | EC$_{50}$ | CC$_{50}$ | Rat liver microsomes t ½ (min) | Permeability (1e$^{-6}$ cm/s) | Sol. (µg/mL) |
|---|---|---|---|---|---|---|---|
| 36 | 9-anthracenyl | (3,5-dimethylpiperidin-1-yl)propylamino | 0.214 | 4.27 | 22 | ND | 62.1 |
| 37 | 2,6-dimethoxyphenyl | (3,5-dimethylpiperidin-1-yl)propylamino | 3.339 | >31.6 | 12 | ND | >76.0 |
| 38 | 2-methoxy-6-fluorophenyl | (3,5-dimethylpiperidin-1-yl)propylamino | 0.455 | >31.6 | 8.6 | ND | >74.0 |
| 39 | 2-methylnaphthalen-1-yl | (3,5-dimethylpiperidin-1-yl)propylamino | 0.124 | 4.08 | 4.9 | 547.1 | >76.0 |
| 40 | 2-methoxy-6-bromophenyl | (3,5-dimethylpiperidin-1-yl)propylamino | 0.213 | 14.9 | 3.5 | 245.3 | >83.0 |
| 41 | 2,6-dichlorophenyl/dibromo | (3,5-dimethylpiperidin-1-yl)propylamino | 0.178 | 12.2 | 1.4 | ND | >83.0 |
| 42 | 2-methoxy-6-chlorophenyl | (3,5-dimethylpiperidin-1-yl)propylamino | 0.137 | 15.8 | 3.3 | 51.0 | >76.0 |

TABLE 1-continued

| | Ar | A | EC$_{50}$ | CC$_{50}$ | Rat liver microsomes t ½ (min) | Permeability (1e$^{-6}$ cm/s) | Sol. (µg/mL) |
|---|---|---|---|---|---|---|---|
| 43 | 2,6-dibromophenyl | N-propyl-(3,5-dimethylpiperidinyl) | 0.386 | 6.51 | 2.1 | <1.0 | 62.4 |
| 44 | 2-Cl-6-CF$_3$-phenyl | N-propyl-(3,5-dimethylpiperidinyl) | 0.354 | 12.2 | 1.8 | ND | 65.1 |
| 45 | 2-OMe-6-Me-phenyl | N-propyl-(3,5-dimethylpiperidinyl) | 0.423 | 14.8 | 4.6 | 197.7 | >73.0 |
| 46 | 2-F-6-Me-phenyl | N-propyl-(3,5-dimethylpiperidinyl) | 0.311 | 13 | 4.4 | 233.8 | >72.0 |
| 47 | 2-Me-phenyl | N-propyl-(3,5-dimethylpiperidinyl) | 0.050 | 9.390 | 14 | 553.7 | >69.0 |
| 48 | 2-Me-phenyl | N-propyl-(3,5-diethylpiperidinyl) | 0.181 | 3.467 | 5.5 | 1267 | ND |
| 49 | 2-Me-phenyl | N-propyl-(3,3,5,5-tetramethylpiperidinyl) | 0.083 | 5.7 | >1397 | ND | |

TABLE 1-continued
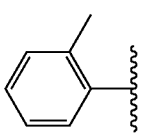 [SMILES: *c1ccccc1C]
| | Ar | A | EC$_{50}$ | CC$_{50}$ | Rat liver microsomes t ½ (min) | Permeability (1e$^{-6}$ cm/s) | Sol. (μg/mL) |
|---|---|---|---|---|---|---|---|
| 50 | 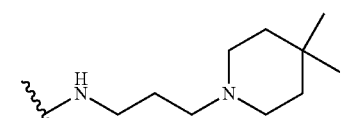 | 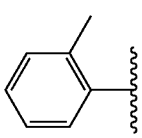 [SMILES: *c1ccccc1C] | 0.066 | 10.2 | >30.0 | 241.4 | >69.0 |
| 51 | 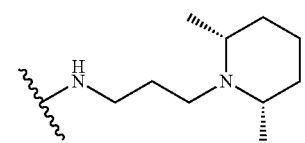 | 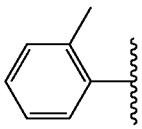 [SMILES: *c1ccccc1C] | 0.120 | 21.3 | .30.0 | 55.4 | >69.0 |
| 52 |  | 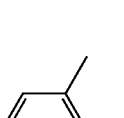 | 0.054 | 5.823 | 19.4 | Nd | >71 |
| 53 |  |  | 0.094 | 4.64 | 2.3 | 3 | 54.9 |
| 54 | 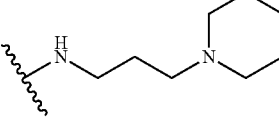 | 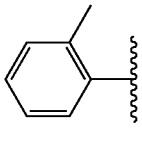 [SMILES: *c1ccccc1C] | 0.106 | 10.87 | 7.4 | 330.9 | .71 |
| 55 | 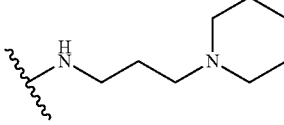 | 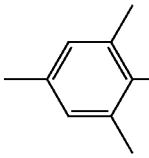 | 0.190 | 6.573 | >30 | ND | ND |
| 56 | 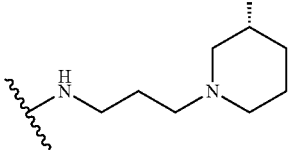 | | 0.149 | 8.183 | ND | 455.2 | ND |

TABLE 1-continued

| | Ar | A | EC$_{50}$ | CC$_{50}$ | Rat liver microsomes t ½ (min) | Permeability (1e$^{-6}$ cm/s) | Sol. (μg/mL) |
|---|---|---|---|---|---|---|---|
| 57 | 4-F-phenyl | (3,5-dimethylpiperidin-1-yl)propylamino | 0.053 | 12.8 | 28.1 | ND | ND |
| 58 | 3,4-diCl-phenyl | (3,5-dimethylpiperidin-1-yl)propylamino | 0.013 | 3.17 | >30 | 552 | ND |
| 59 | 2-Cl-6-methyl-phenyl | (3-methylpiperidin-1-yl)propylamino | 0.370 | 16.4 | 5.4 | 650.6 | 52.6 |
| 60 | 2-Cl-6-methyl-phenyl | (4,4-dimethylpiperidin-1-yl)propylamino | 0.220 | 11.7 | 4.4 | ND | >74 |
| 61 | 2-Cl-6-methyl-phenyl | (4-isopropylpiperidin-1-yl)propylamino | 0.124 | 4.91 | 2 | ND | >76 |
| 62 | 2-methyl-naphthalen-1-yl | (3,5-dimethylpiperidin-1-yl)propylamino | 0.097 | 4.06 | 4.9 | 547.1 | >76.1 |

TABLE 1-continued

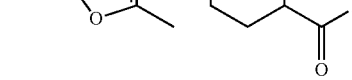

| | Ar | A | EC$_{50}$ | CC$_{50}$ | Rat liver microsomes t ½ (min) | Permeability (1e$^{-6}$ cm/s) | Sol. (µg/mL) |
|---|---|---|---|---|---|---|---|
| 63 | 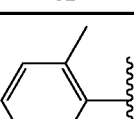 | 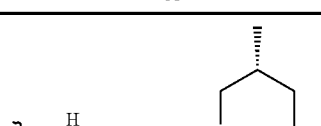<br>(+)-Isomer | 0.084 | 14.2 | 7.6 | 497.7 | 54.8 |
| 64 | 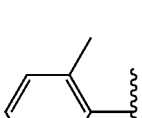 | 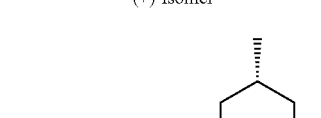<br>(−)-Isomer | 0.094 | 14.0 | 7.3 | ND | >69.0 |

Example 7

This example demonstrates the EC$_{50}$ and CC$_{50}$ values against HCV according to the HCVcc-RLuc reporter assay described in Example 5 and the cytotoxicity using the Huh 7.5.1 ATPlite assay for compounds in accordance with an embodiment of the invention. The results are set forth in Table 2. Table 2 further contains data on the rat liver microsome assay, cell permeability, and solubility.

TABLE 2

| | Compound | EC$_{50}$ | CC$_{50}$ | Rat liver microsomes t ½ (min) | Permeability (1e$^{-6}$ cm/s) | Sol. (µg/mL) |
|---|---|---|---|---|---|---|
| 65 | | 0.038 | 7.1 | 7.4 | ND | >71.0 |

TABLE 2-continued

| Compound | EC$_{50}$ | CC$_{50}$ | Rat liver microsomes t ½ (min) | Permeability (1e$^{-6}$ cm/s) | Sol. (μg/mL) |
|---|---|---|---|---|---|
| 66 | 0.41 | 13.3 | 3.9 | 864.8 | 57.8 |
| 67 (R)-enantiomer | 0.304 | 13.3 | 3.9 | 864.8 | 57.8 |
| 68 | 0.153 | 39.1 | 16.4 | 1061 | 2.5 |

TABLE 2-continued

| Compound | EC$_{50}$ | CC$_{50}$ | Rat liver microsomes t ½ (min) | Permeability (1e$^{-6}$ cm/s) | Sol. (μg/mL) |
|---|---|---|---|---|---|
| 69 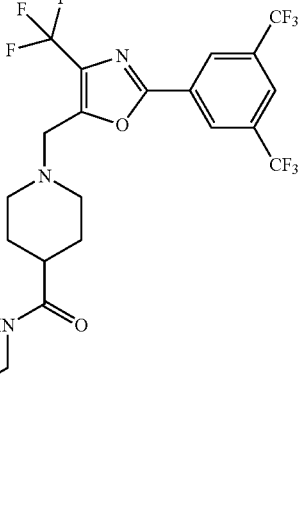 | 0.341 | 8.19 | 5.7 | >1397 | ND |
| 70 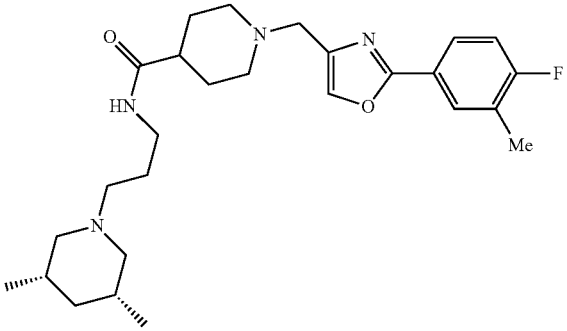 [SMILES: Cc1cc(-c2nc(CN3CCC(C(=O)NCCCN4C[C@H](C)C[C@H](C)C4)CC3)co2)ccc1F] | 0.038 | 12.97 | 14.1 | 215.4 | >70 |
| 71 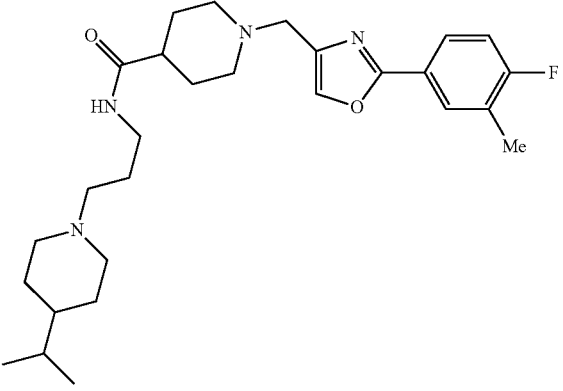 [SMILES: Cc1cc(-c2nc(CN3CCC(C(=O)NCCCN4CCC(C(C)C)CC4)CC3)co2)ccc1F] | 0.055 | 6.195 | 2.5 | 276.4 | >72 |

Example 8

This example demonstrates cell based assays in accordance with an embodiment of the invention.

To investigate the stages of virus life cycle where compounds of the invention act on, HCV single-cycle infection assay, HCV subgenomic replicon assays and HCV pseudoparticle (HCVpp) assays were performed.

A. Huh 7.5.1 cells seeded in 96-well plates (10$^4$ cells/well) were cultured overnight. The cells were inoculated with the infectious HCVsc together with the tested compounds. Luciferase activity of the cells was measured 48 h after the compound treatment.

B. HCV subgenomic replicon assays. HCV replicon (GT 1b and 2a) cells were plated into 96-well plate (10$^4$ cells/well) and incubated overnight. The cells were treated with tested compounds. Luciferase activity of the cells was measured 48 h after the compound treatment. In transient replicon assay, Huh 7.5.1 cells seeded in 96-well plates ($10^4$ cells/well) were cultured overnight. Then the cells were transiently transfected with the replicon mRNA with DMRIE-C for 4 h. After removing the transfection reagent, the cells were incubated with DMEM culture medium containing 10 μM of each compound for 48 h. Luciferase activity was measured.

C. HCVpp assays. Huh 7.5.1 cells were seeded in 96-well plates ($10^4$ cells/well) and cultured overnight. Then the cells were treated with 10 μM of the compounds together with infection of HCVpp GT 1a, 1b, VSVpp and MLVpp for 4 h. The cells were then washed and cultured for 48 h followed by a luciferase assay to detect the HCV entry. The results shown are the means of at least five replicates±SEM. Cyclosporin A and rottlerin at 10 μM were used as positive controls.

In HCV single-cycle infection assay (Masaki, T. et al., *J. Virology*, 2010, 84: 5824-5835), the single round infectious HCV defective particle (HCVsc, genotype 2a) were used to infect Huh 7.5.1 cells. The HCVsc can infect and replicate but does not assemble new virions, thus this assay detects compounds with inhibitory activity to HCV life cycle events prior to assembly. HCV subgenomic replicon assays evaluate whether compounds target viral RNA replication. HCVpp (GT 1a and 1b) are defective retroviral particles that display HCV envelope glycoproteins, and they are used to assess the effect of compound treatment on viral entry. VSVpp and MLVpp were also tested in the entry assay as control viruses for virus selectivity.

Example 9

This example demonstrates mechanism of action studies of compound 3, in accordance with an embodiment of the invention.

To determine the target of this chemotype in the viral life cycle, HCV single-cycle infection assays, HCV subgenomic replicon assays and HCV pseudoparticle (HCVpp) assays were performed with the hit compound 3 at 10 μM. In the HCV single-cycle infection assay, single round infectious HCV defective particles (HCVsc, genotype 2a) were used to infect Huh7.5.1 cells. The HCVsc can infect and replicate but does not assemble new virions, thus this assay detects compounds with inhibitory activity to HCV life cycle events prior to assembly. Compound 3 caused dramatic inhibitory activities in the HCVsc infection level, suggesting this chemotype targets an early stage of the viral life cycle. HCV subgenomic replicon assays evaluate whether compounds target viral RNA replication. Compound 3 showed no inhibitory effect on HCV replication in either transient transfection assay with GT 2a replicon RNA or GT 2a replicon cell line. This implicates that the replication stage is less likely to be the target of this chemotype. On the other hand, HCVpp (GT 1a and 1b) are defective retroviral particles that display HCV envelope glycoproteins, which have been used to assess the effect of compound treatment on viral entry. Viral pseudo particles from vesicular stomatitis virus (VSVpp) were also tested using compound 3 as a control for virus selectivity. Compound 3 showed potent inhibitory activity (<30% RLU of control) in HCVpp GT 1a assay and moderate inhibition (~50% RLU) in VSVpp assay. Overall, the results for SID 144187742 (CID3244725) in HCV life cycle assays suggest that the chemotype is targeting an early stage of the viral life cycle and showed potent inhibitory activity on HCV entry. The results are set forth in Table 3.

TABLE 3

| HCV life cycle assay | HCVsc | HCV subgenomic replicon | | HCVpp | |
| --- | --- | --- | --- | --- | --- |
| | | Transient GT 2a | GT 2a cell line | GT 1a | VSV pp |
| % RLU at 10 μM | 1.63 ± 1.57 | 105 ± 15.3 | 103 ± 4.38 | 21.9 ± 14.7 | 48.7 ± 3.85 |

Note: In HCV single-cycle infection assay, Huh7.5.1 cells seeded in 96-well plates ($10^4$ cells/well) were cultured overnight. The cells were inoculated with the infectious HCVsc together with the tested compounds. Luciferase activity of the cells was measured 48 h after the compound treatment. In transient replicon assay, Huh7.5.1 cells seeded in 96-well plates ($10^4$ cells/well) were cultured overnight. Then the cells were transiently transfected with the replicon RNA transcript with DMRIE-C for 4 h. After removing the transfection reagent, the cells were incubated with DMEM culture medium containing 10 μM of each compound for 48 h. Luciferase activity was measured. In HCV subgenomic replicon assay with HCV replicon (GT 2a) cells, cells were plated into 96-well plate ($10^4$ cells/well) and incubated overnight. The cells were treated with tested compounds. Luciferase activity was measured 48 h after the compound treatment. In HCVpp assays, Huh7.5.1 cells were seeded in 96-well plates ($10^4$ cells/well) and cultured overnight. Then the cells were treated with 10 μM of the compounds together with infection of HCVpp GT 1a or VSVpp for 4 h. The cells were then washed and cultured for 48 h followed by a luciferase assay to detect the HCV entry. The results shown are the means of five replicates±SEM. Combination of ribavirin and peginterferon α (IFN-α) has been the standard of care to treat chronic HCV infection for many years. Direct-acting antivirals, such as telaprevir and daclatasvir, were recently approved for therapy of hepatitis C. Here the combination of compound 3 with these different classes of anti-HCV drugs was investigated. HCVcc-RLuc assay in parallel with ATPlite assay was performed in the presence of various concentrations of compound 3 in combination with various concentrations of each drug. The combination of compound 3 and each drug led to a greater HCV inhibitory effect than either of them alone in a dose-dependent manner without toxic effect on cell viability. Log volumes of synergy or antagonism were generated according to the Bliss independence model by using the MacSynergy II program, and the synergy volumes are summarized in Table 4.

TABLE 4

| Program | Parameter | Ribavirin | IFN-α | Telaprevir | Daclatasvir | Cyclosphorin A | 2'-C-methylcytidine |
| --- | --- | --- | --- | --- | --- | --- | --- |
| CalcuSyn | CI value[a] | 0.770 ± 0.189 | 0.545 ± 0.052 | 0.775 ± 0.108 | 0.510 ± 0.082 | 0.625 ± 0.136 | 1.10 ± 0.10 |
| | Synergy volume[b] | ++ | +++ | ++ | +++ | +++ | +/− |

TABLE 4-continued

| Program | Parameter | Ribavirin | IFN-α | Telaprevir | Daclatasvir | Cyclosphorin A | 2'-C-methylcytidine |
|---|---|---|---|---|---|---|---|
| MacSynergy | Synergy volume[c] | +++ | + | +++ | + | ++ | +++ |

[a]Values are mean ± SEM of combination indexes (CI) obtained from combinations of the tested drug with SID 144187742 (CID 3244725) at or near their EC50 values when tested alone (n ≥ 6).
[b]The level of synergy is defined as the following: "+/−" means nearly additive (0.9 < CI < 1.1), "++" means moderate synergy (0.7 < CI < 0.85) and "+++" means synergy (0.3 < CI < 0.7).
[c]The levels of synergy are defined as the following: "++" means moderate synergy (5 < log volume < 9) and "+++" means strong synergy (log volume > 9).

The results were also analyzed with CalcuSyn program, in which the combination indexes were calculated from combination of compound 3 and the tested drug at or near their EC50 values when tested alone. Overall, the antiviral effect of compound 3 is synergistic with ribavirin, interferon-γ, telaprevir (NS3/4A inhibitor), daclatasvir (NS5A inhibitor), cyclosporin A, and 2'-C-methylcytidine (NS5B inhibitor), without significant cytotoxicity, supporting its use in combination therapy with these drugs. The observed synergistic effects suggest that this chemotype inhibits HCV infection through a different mechanism from any one of these drugs. The mechanism of action of ribavirin and IFN-α is mediated through host antiviral response. Telaprevir is NS3/4A protease inhibitor and daclatasvir inhibits HCV NS5A. Cyclosporin A targets virus RNA replication and 2'-C-methylcytidine is a NS5B polymerase inhibitor. The synergistic effect of compound 3 with these reagents suggests that its mechanism of action is novel and unique. This makes this chemotype attractive for development with a possibly unique mechanism and lower probability of selecting resistant virus strains during treatment.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound selected from:

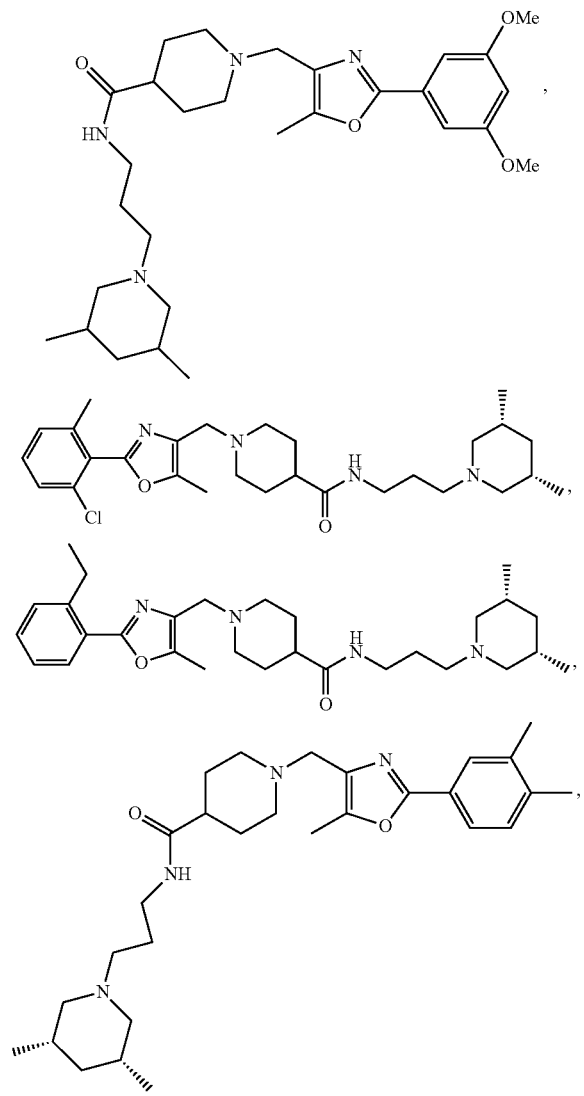

71
-continued
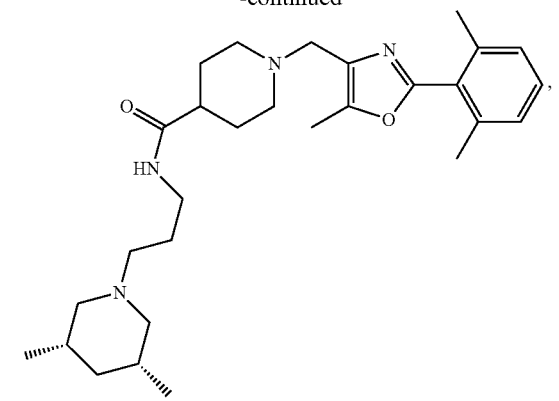
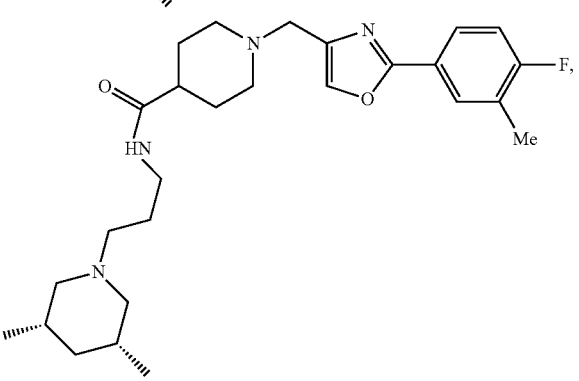
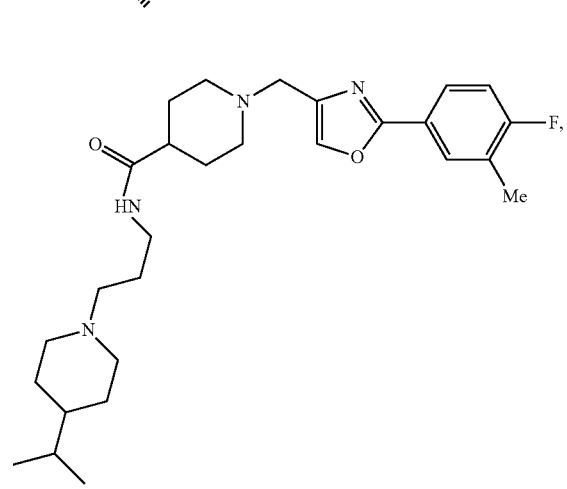
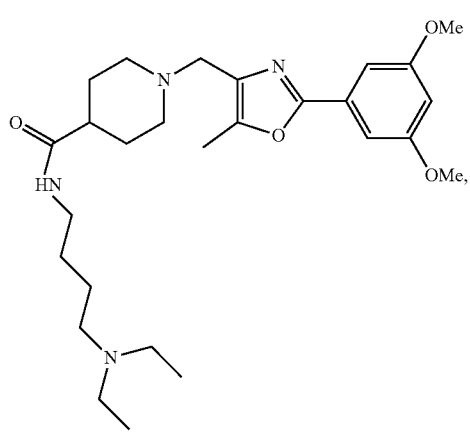
72
-continued
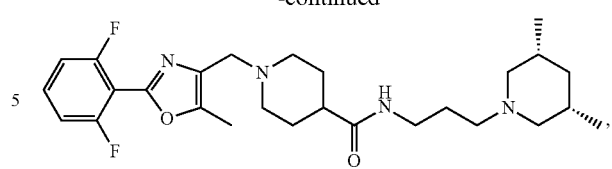
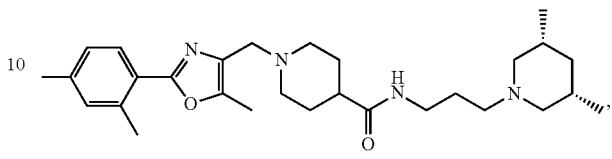
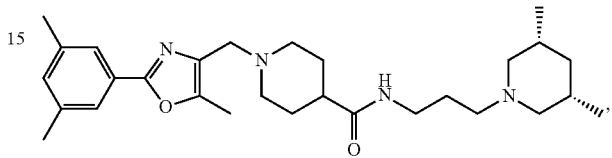
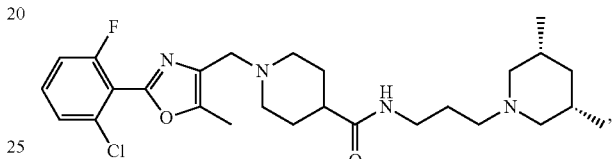
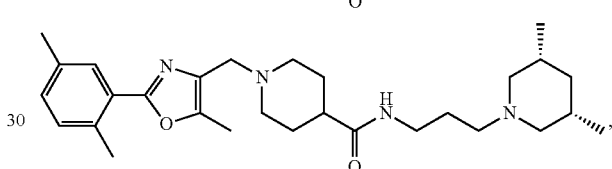
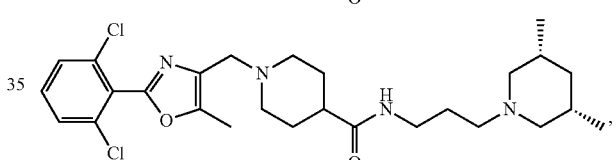
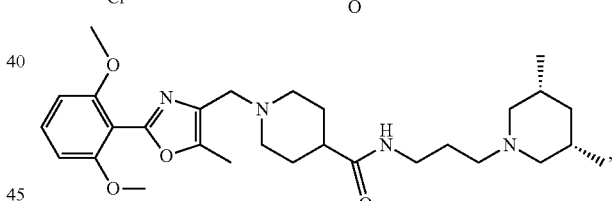
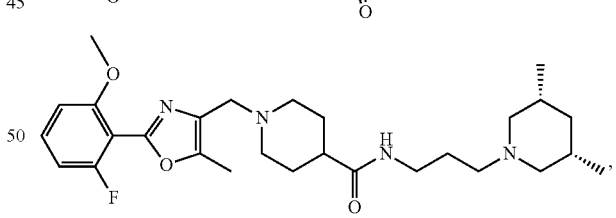
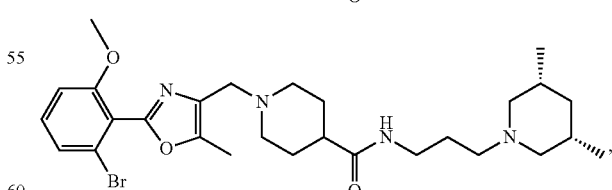
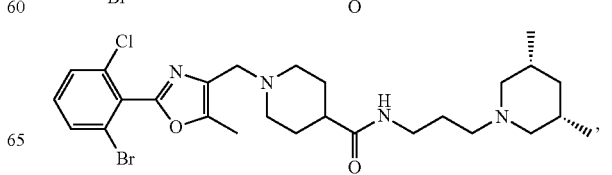

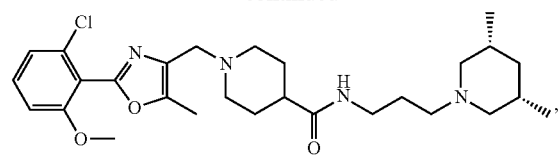
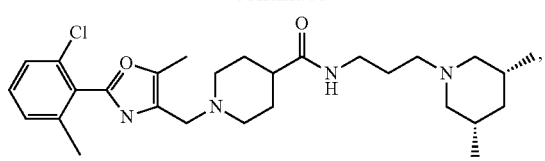
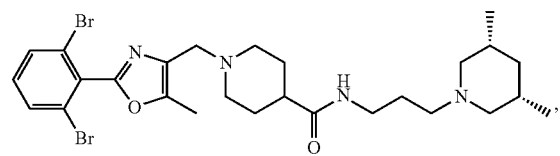
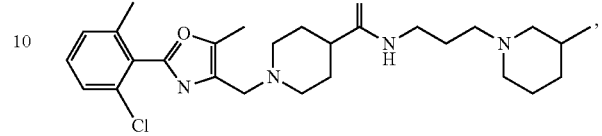
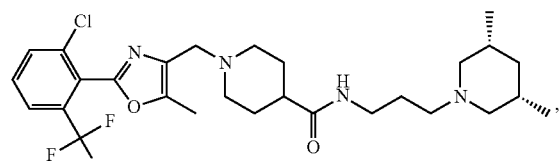
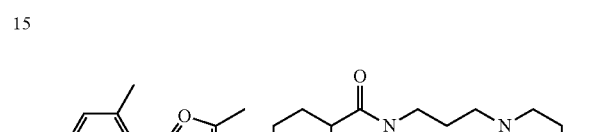
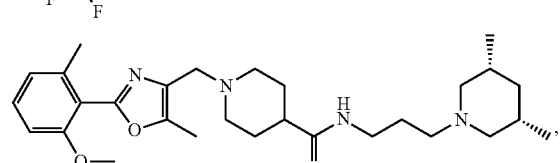
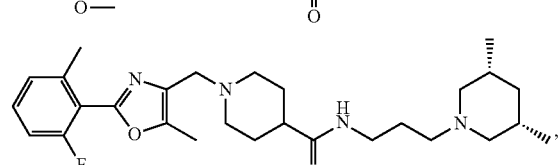
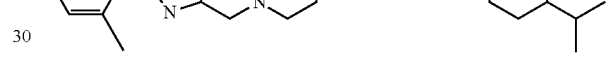
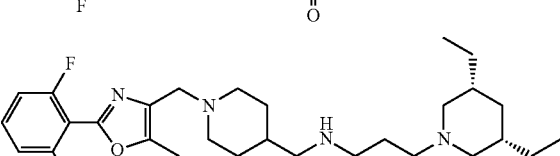
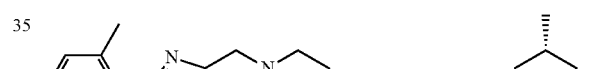
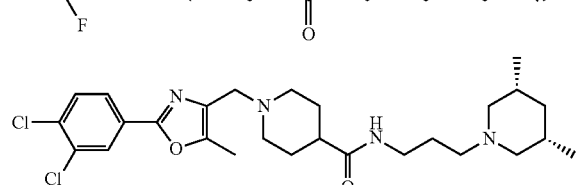
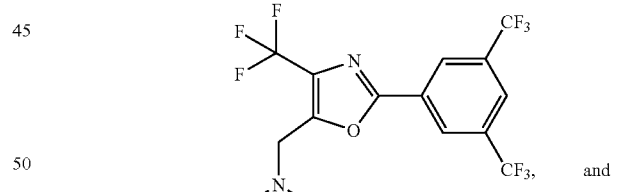
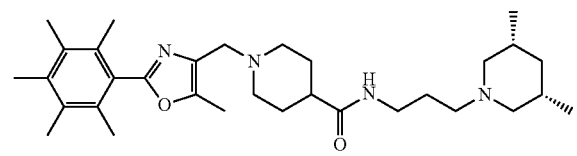
and
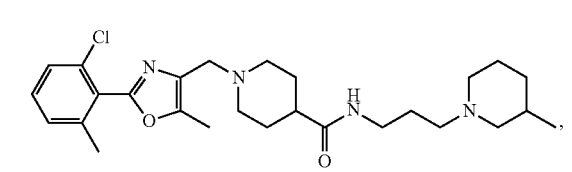
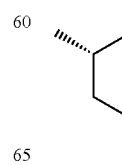

-continued

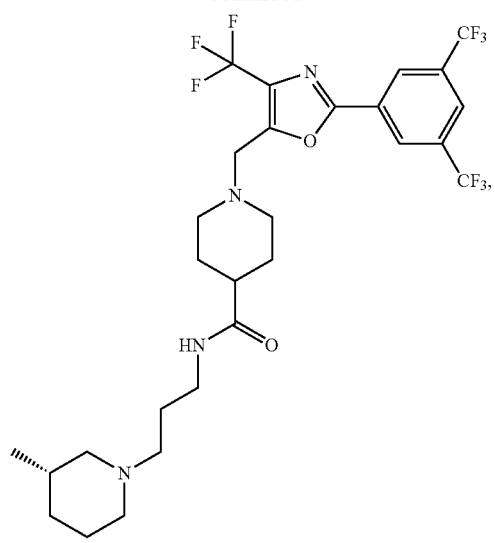

or a pharmaceutically acceptable salt thereof, stereoisomer thereof, or mixture comprising stereoisomers thereof.

2. A pharmaceutical composition comprising a compound, salt, stereoisomer, or a mixture of stereoisomers of claim 1 and a pharmaceutically acceptable carrier.

3. A kit comprising:
(a) a compound of claim 1, and
(b) at least one anti-hepatitis C compound other than the compound of claim 1.

4. A compound selected from:

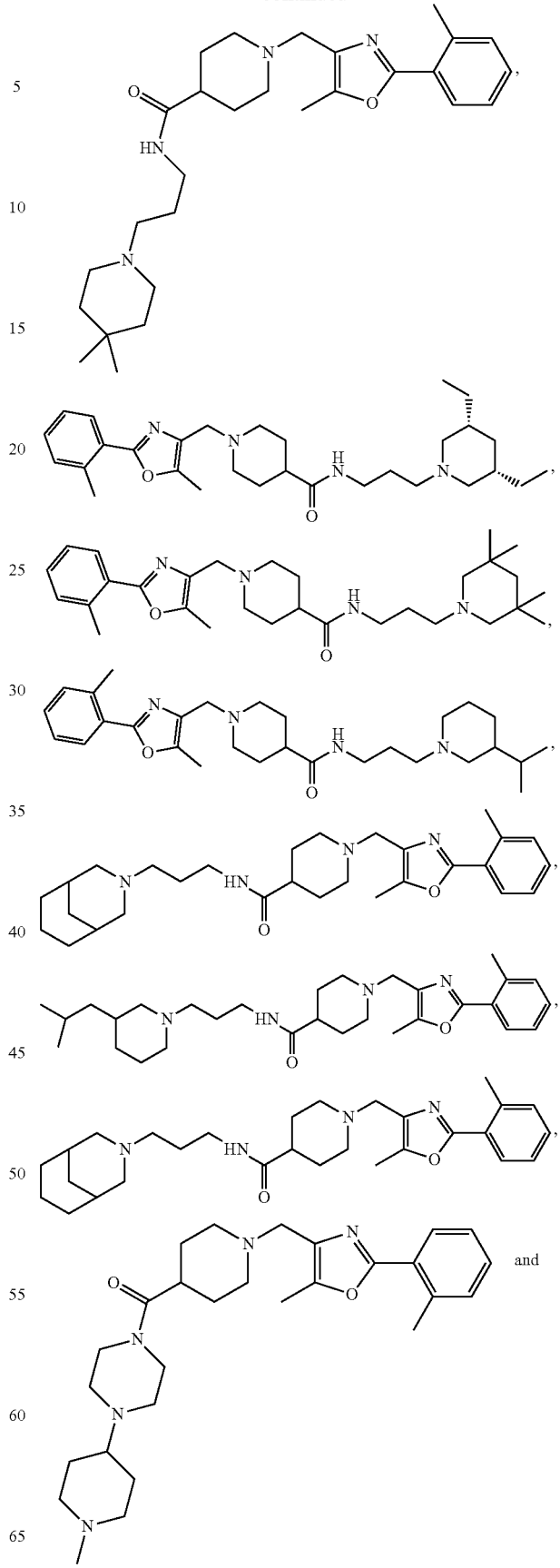

-continued
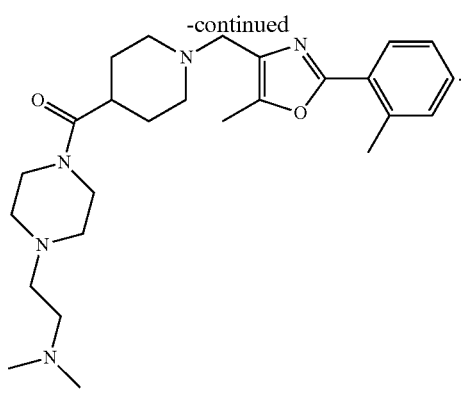
5. A pharmaceutical composition comprising a compound, salt, stereoisomer, or a mixture of stereoisomers of 4 and a pharmaceutically acceptable carrier.
6. A kit comprising:
(a) a compound of claim 4, and
(b) at least one anti-hepatitis C compound other than the compound of claim 4.
* * * * *